United States Patent

Nam et al.

(10) Patent No.: US 9,839,403 B2
(45) Date of Patent: Dec. 12, 2017

(54) MEDICAL IMAGING APPARATUS AND METHOD FOR PROCESSING MEDICAL IMAGE

(71) Applicant: Samsung Electronics Co., Ltd., Suwon-si (KR)

(72) Inventors: Woo-hyun Nam, Seoul (KR); Yong-sup Park, Seoul (KR); Jae-sung Lee, Seoul (KR); Yun-sub Jung, Yongin-si (KR); Yoon-mi Hong, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 77 days.

(21) Appl. No.: 14/956,237

(22) Filed: Dec. 1, 2015

(65) Prior Publication Data

US 2016/0151036 A1 Jun. 2, 2016

(30) Foreign Application Priority Data

Dec. 1, 2014 (KR) .................. 10-2014-0169972

(51) Int. Cl.
*G06K 9/00* (2006.01)
*A61B 6/00* (2006.01)
*G06T 11/00* (2006.01)
*A61B 6/03* (2006.01)

(52) U.S. Cl.
CPC ............ *A61B 6/469* (2013.01); *A61B 6/4441* (2013.01); *A61B 6/5205* (2013.01); *G06T 11/005* (2013.01); *A61B 6/037* (2013.01); *A61B 6/488* (2013.01); *G06T 2211/424* (2013.01); *G06T 2211/432* (2013.01)

(58) Field of Classification Search
None
See application file for complete search history.

(56) References Cited

U.S. PATENT DOCUMENTS

| 6,768,782 | B1 * | 7/2004 | Hsieh ............ A61B 6/032 378/4 |
| 7,444,010 | B2 | 10/2008 | De Man |
| 8,433,119 | B2 | 4/2013 | Deykoon |

(Continued)

FOREIGN PATENT DOCUMENTS

| KR | 10-2009-0078513 | 10/2009 |
| WO | 2012093364 A1 | 7/2012 |

OTHER PUBLICATIONS

Leng, Shuai, et al., Exact fan-beam image reconstruction algorithm for truncated projection data acquired from an asymmetric half-size detector, Phys. Med. Biol. 50 (2005) 1805-1820.

(Continued)

Primary Examiner — Shervin Nakhjavan
(74) Attorney, Agent, or Firm — McAndrews, Held & Malloy, Ltd.

(57) ABSTRACT

A medical imaging apparatus includes a data acquirer configured to acquire measured data acquired by detecting an X-ray transmitted by an X-ray source to an object, and an image processor configured to acquire an initial image based on the measured data, alternately estimate region of interest (ROI)-outside measured data and ROI-inside measured data based on the measured data and the initial image, and acquire a reconstructed image based on the ROI-inside measured data.

35 Claims, 27 Drawing Sheets

(56) References Cited

U.S. PATENT DOCUMENTS

| | | | |
|---|---|---|---|
| 8,625,870 B2 | 1/2014 | Lamyatin et al. | |
| 2001/0028696 A1* | 10/2001 | Yamada | G06T 11/005 378/4 |
| 2005/0249432 A1 | 11/2005 | Lou et al. | |
| 2007/0100226 A1* | 5/2007 | Yankelevitz | A61B 5/1075 600/407 |
| 2008/0181481 A1* | 7/2008 | Hong | G06T 7/12 382/132 |
| 2009/0010516 A1* | 1/2009 | Boese | A61B 90/36 382/131 |
| 2009/0060121 A1* | 3/2009 | Ziegler | A61B 6/032 378/8 |
| 2009/0196393 A1* | 8/2009 | Wang | G06T 11/006 378/4 |
| 2011/0105880 A1 | 5/2011 | Yu et al. | |
| 2011/0116594 A1* | 5/2011 | Yamakawa | A61B 6/032 378/19 |
| 2011/0282181 A1* | 11/2011 | Wang | A61B 5/0095 600/407 |
| 2012/0063659 A1 | 3/2012 | Wang et al. | |
| 2012/0101733 A1 | 4/2012 | Han et al. | |
| 2012/0141006 A1 | 6/2012 | Koehler et al. | |
| 2012/0297872 A1* | 11/2012 | Kaiser | B25J 9/1674 73/492 |
| 2013/0294570 A1 | 11/2013 | Hansis | |
| 2014/0135623 A1* | 5/2014 | Manak | A61B 8/4416 600/427 |
| 2016/0151036 A1* | 6/2016 | Nam | A61B 6/5205 378/62 |

OTHER PUBLICATIONS

Int'l Search Report and Written Opinion for PCT/KR2012/012952 dated Mar. 7, 2016.

* cited by examiner

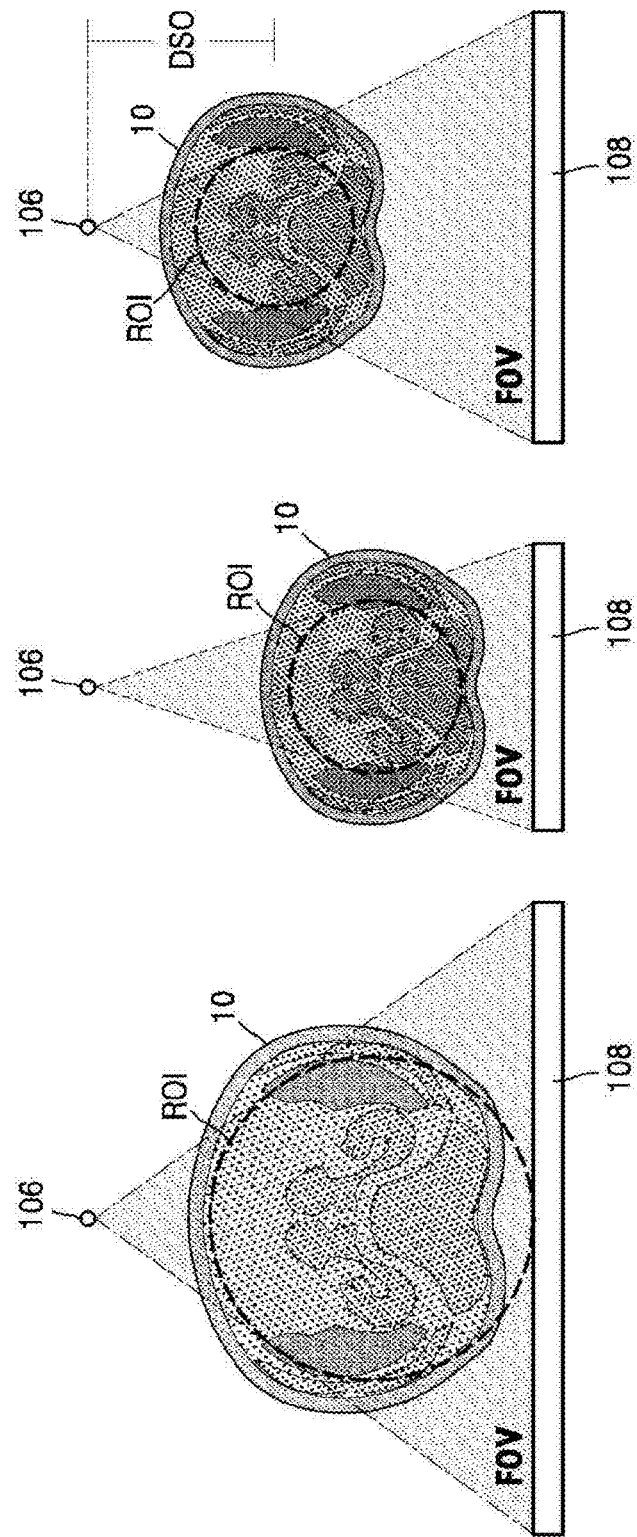

FIG. 14
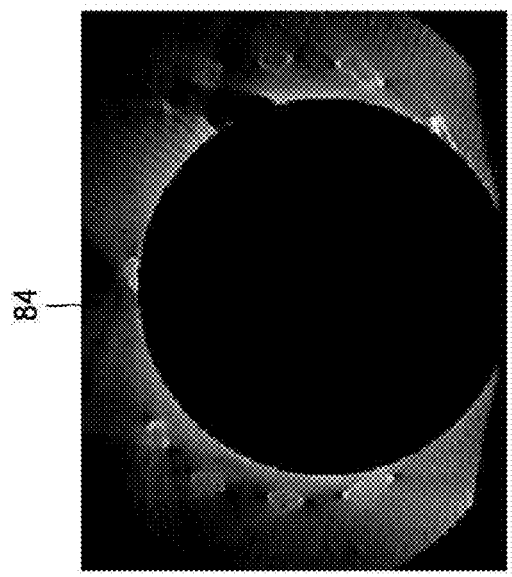
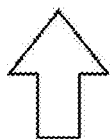
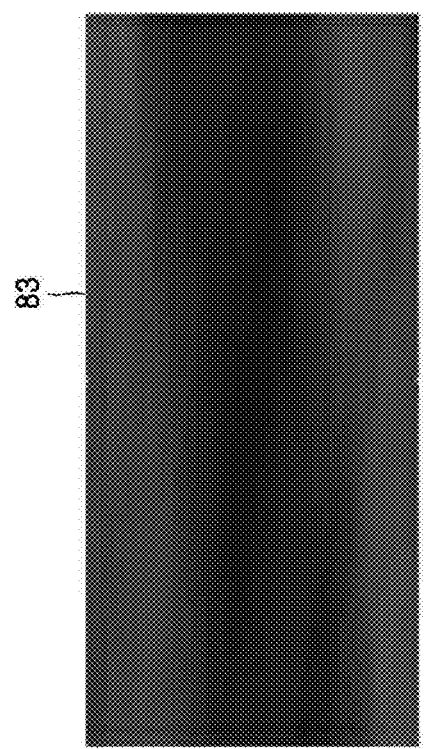

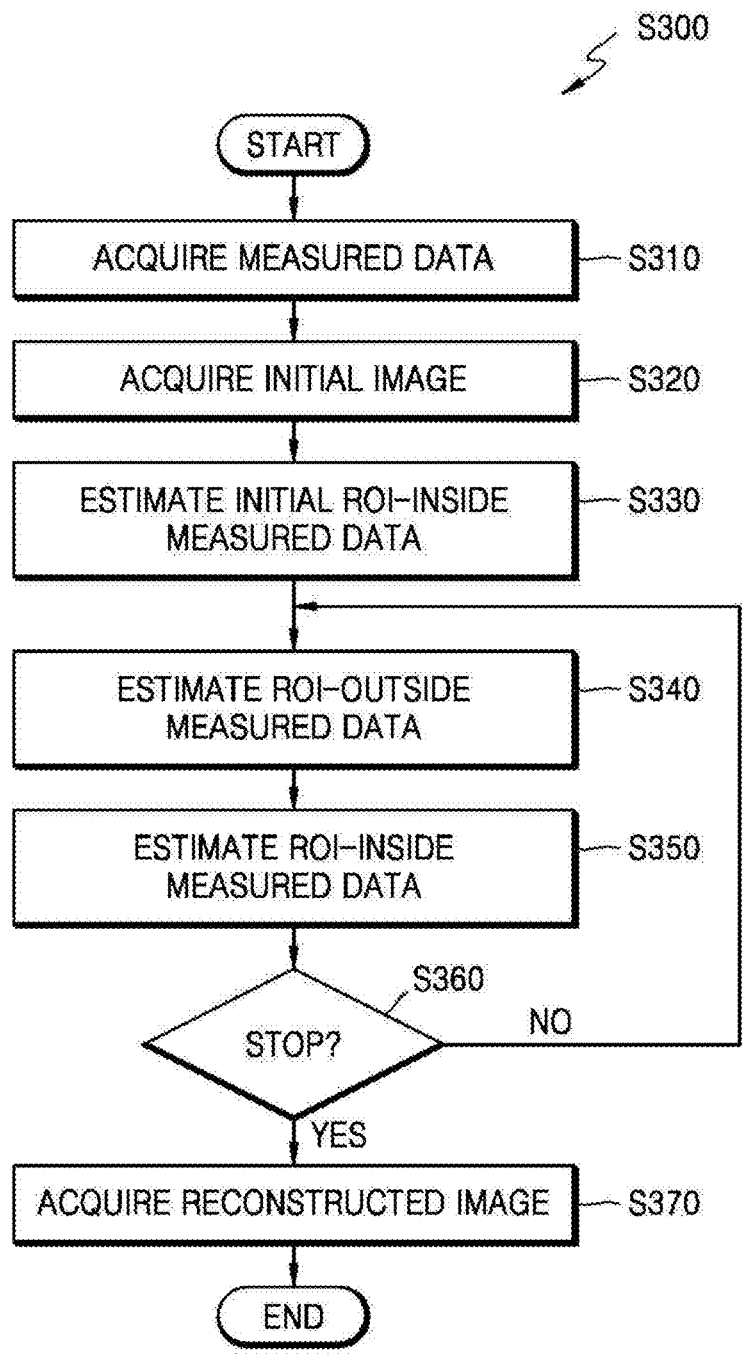

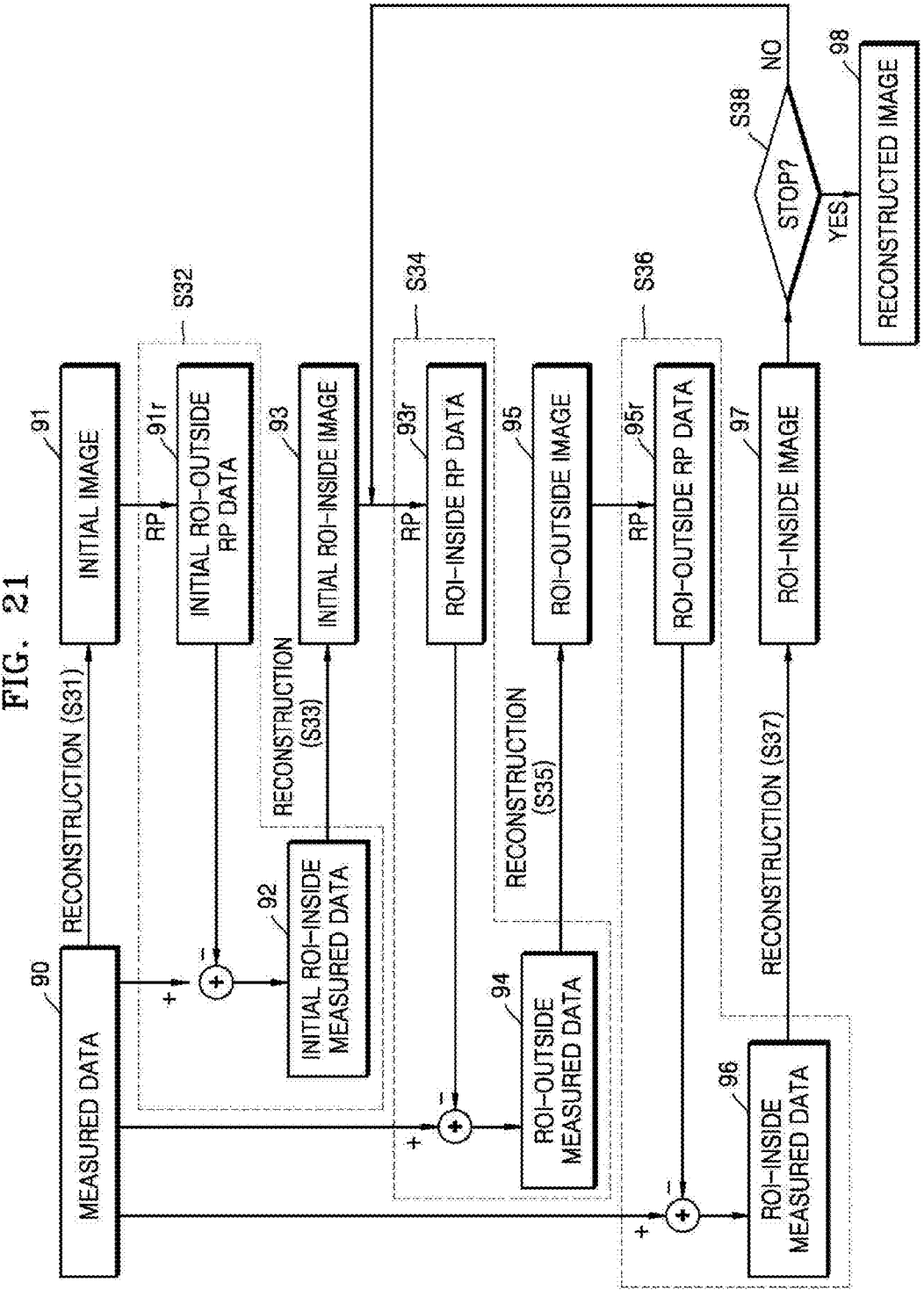

MEDICAL IMAGING APPARATUS AND METHOD FOR PROCESSING MEDICAL IMAGE

RELATED APPLICATION(S)

This application claims the benefit of Korean Patent Application No. 10-2014-0169972, filed on Dec. 1, 2014, in the Korean Intellectual Property Office, the disclosure of which is incorporated herein in its entirety by reference.

BACKGROUND

Present disclosure relates to a medical imaging apparatus and a method of processing a medical image, and more particularly, to a medical imaging apparatus and a method of processing a medical image to alleviate image deterioration.

A medical imaging apparatus is used to acquire an image of an internal structure of an object. The medical imaging apparatus, which is a non-invasive test apparatus, provides a user with medical information by imaging and processing structural details, internal tissues, or a fluid flow in a human body. A user, such as a medical doctor, may check and diagnose the health and disease state of a patient based on medical images from a medical imaging apparatus.

A typical medical imaging apparatus may be an X-ray apparatus or a computed tomography (CT) apparatus. An X-ray apparatus is a medical apparatus used to acquire an image of an internal structure of a human body by transmitting an X-ray through the human body. Compared to other medical apparatuses such as a magnetic resonance imaging (MRI) apparatus or a CT apparatus, the X-ray apparatus has merit in that a medical image of an object may be acquired within a short time. Accordingly, the X-ray apparatus has been widely used for normal imaging of chest, abdomen, skeleton, sinus, neck soft tissue, and breasts as well as other body parts.

A CT apparatus, which may provide a sectional image of an object, may provide images of internal organs such as kidney or lung, without overlapping them with other organs.

Both the X-ray apparatus and the CT apparatus acquire a medical image by transmitting an X-ray through an object. However, it is known that exposure to high doses of X-ray can damage body parts. Accordingly, a medical imaging apparatus and a method of processing a medical image whereby a high quality medical image may be acquired by exposing the object to a reduced amount of X-rays are needed.

SUMMARY

One or more exemplary embodiments include a medical imaging apparatus and a method of processing a medical image, which may improve quality of a medical image Additional aspects will be set forth in part in the description which follows and, in part, will be apparent from the description, or may be learned by practice of the presented exemplary embodiments.

According to one or more exemplary embodiments, a medical imaging apparatus includes a data acquirer configured to acquire measured data acquired by detecting X-ray transmitted by an X-ray source to an object, and an image processor configured to acquire an initial image based on the measured data, estimate a region of interest (ROI)-outside measured data and an ROI-inside measured data based on the measured data and the initial image, and acquire a reconstructed image based on the ROI-inside measured data.

The image processor may be further configured to estimate a difference between data acquired by re-projecting an inside of an ROI in the initial image and the measured data as the ROI-outside measured data, and acquire an ROI-outside image based on the ROI-outside measured data and estimate a difference between data acquired by re-projecting the ROI-outside image and the measured data as the ROI-inside measured data.

The image processor may be further configured to acquire an ROI-inside image based on the ROI-inside measured data, determine whether to update the ROI-outside measured data and the ROI-inside measured data, and when it is determined to update the ROI-outside measured data and the ROI-inside measured data, the image processor updates the ROI-outside measured data based on the ROI-inside image, the ROI-inside measured data based on the updated ROI-outside measured data, and the ROI-inside image based on the updated ROI-inside measured data.

The image processor may be further configured to iteratively perform an update operation including updating the ROI-outside measured data, updating the ROI-inside measured data, and updating the ROI-inside image until it is determined to stop updating the ROI-outside measured data and the ROI-inside measured data, and acquire the reconstructed image based on a finally updated ROI-inside image, where the finally updated ROI-inside image is the ROI-inside image updated just prior to being determined to stop updating the ROI-outside measured data and the ROI-inside measured data.

The image processor may be configured to stop the update operation when a difference between the ROI-inside measured data and data acquired by re-projecting the ROI-inside image acquired based on the ROI-inside measured data is less than a threshold value.

The image processor may be configured to stop the update operation after repeating the update operation a predetermined number of times.

The medical imaging apparatus may further include an input unit configured to receive an input for determining the predetermined number of times for repeating the update operation.

The medical imaging apparatus may further include an output unit configured to output at least one of the ROI-inside image and the updated ROI-inside image, and an input unit configured to receive an input as to whether the output ROI-inside image is approved, wherein when the input received through the input unit indicates that the output ROI-inside image is approved, the image processor stops the update operation.

The medical imaging apparatus may further include an input unit configured to receive a parameter related to estimation or updating the ROI-outside measured data.

The image processor may be further configured to acquire the ROI-outside image based on the ROI-outside measured data by an iterative reconstruction technique and acquire the ROI-inside image based on the ROI-inside measured data by the iterative reconstruction technique.

The image processor may be further configured to acquire the initial image based on the measured data by using at least one of an analytical reconstruction technique and an iterative reconstruction technique.

The image processor may be further configured to acquire the initial image by removing an outside of the ROI from an image reconstructed based on the measured data.

The image processor may be further configured to estimate a difference between data acquired by re-projecting an outside of an ROI in the initial image and the measured data as initial ROI-inside measured data, acquire an initial ROI-inside image based on the initial ROI-inside measured data and estimate a difference between data acquired by re-projecting the ROI-inside image and the measured data as the ROI-outside measured data, and acquire an ROI-outside image based on the ROI-outside measured data and estimate a difference between data acquired by re-projecting the ROI-outside image and the measured data as the ROI-inside measured data.

The image processor is configured to acquire an ROI-inside image based on the ROI-inside measured data, determine whether to update the ROI-outside measured data and the ROI-inside measured data, and when it is determined to update the ROI-outside measured data and the ROI-inside measured data, the image processor updates the ROI-outside measured data based on the ROI-inside image, the ROI-inside measured data based on the updated ROI-outside measured data, the ROI-inside image based on the updated ROI-inside measured data.

The image processor may be further configured to iteratively perform an update operation including updating the ROI-outside measured data, updating the ROI-inside measured data, and updating the ROI-inside image until it is determined to stop updating the ROI-outside measured data and the ROI-inside measured data, and acquire the reconstructed image based on the finally updated ROI-inside image, wherein the finally updated ROI-inside image is the ROI-inside image updated just prior to being determined to stop updating the ROI-outside measured data and the ROI-inside measured data.

The measured data may be at least one of truncated data and data acquired at a low radiation dose of the X-ray transmitted by the X-ray source, wherein the low radiation dose is less than a reference value.

The medical imaging apparatus may further include a detector configured to rotate with the X-ray source and detect the X-ray.

The medical imaging apparatus may further include a C-arm having one end connected to the X-ray source and another end connected to the detector.

The medical imaging apparatus may further include a gantry including the X-ray source and the detector.

The data acquirer may include a communication unit configured to receive the measured data from a medical apparatus including the X-ray source.

According to one or more exemplary embodiments, a method of operating a medical image apparatus includes acquiring measured data acquired by detecting X-ray transmitted by an X-ray source to an object, acquiring an initial image based on the measured data, estimating a region of interest (ROI)-outside measured data and an ROI-inside measured data based on the measured data and the initial image, and acquiring a reconstructed image based on the ROI-inside measured data.

The estimating of the ROI-outside measured data and ROI-inside measured data may include estimating a difference between data acquired by re-projecting an inside of an ROI in the initial image and the measured data as the ROI-outside measured data, and acquiring an ROI-outside image based on the ROI-outside measured data and estimating a difference between data acquired by re-projecting the ROI-outside image and the measured data as the ROI-inside measured data.

The method may further include acquiring an ROI-inside image based on the ROI-inside measured data, determining whether to update the ROI-outside measured data and the ROI-inside measured data, and when it is determined to update the ROI-outside measured data and the ROI-inside measured data, updating the ROI-outside measured data based on the ROI-inside image, updating the ROI-inside measured data based on the updated ROI-outside measured data, and updating the ROI-inside image based on the updated ROI-inside measured data.

An update operation including updating the ROI-outside measured data, updating the ROI-inside measured data, and updating the ROI-inside image until it is determined to stop updating the ROI-outside measured data and the ROI-inside measured data, and acquire the reconstructed image based on a finally updated ROI-inside image, wherein the finally updated ROI-inside image is the ROI-inside image updated just prior to being determined to stop updating the ROI-outside measured data and the ROI-inside measured data.

The update operation may be stopped when a difference between the ROI-inside measured data and data acquired by re-projecting the ROI-inside image acquired based on the ROI-inside measured data is less than a threshold value.

The update operation may be stopped after the update operation is repeated a predetermined number of times.

The method may further include receiving, from a user, an input about information for determining the predetermined number of times for repeating the update operation.

The method may further include outputting the ROI-inside image or the updated ROI-inside image, and receiving an input as to whether the output ROI-inside image is approved, wherein upon receiving the input indicating that the output ROI-inside image is approved, the image processor stops the update operation.

The method may further include receiving a parameter related to estimation or updating the ROI-outside measured data.

The ROI-outside image may be acquired based on the ROI-outside measured data by an iterative reconstruction technique, and the ROI-inside image may be acquired based on the ROI-inside measured data by the iterative reconstruction technique.

The initial image may be acquired based on the measured data by an analytical reconstruction technique or an iterative reconstruction technique.

The initial image may be acquired by removing an outside of a ROI from an image reconstructed based on the measured data.

The alternately estimating of the ROI-outside measured data and ROI-inside measured data may include estimating a difference between data acquired by re-projecting an outside of ROI in the initial image and the measured data as initial ROI-inside measured data, acquiring an initial ROI-inside image based on the initial ROI-inside measured data and estimating a difference between data acquired by re-projecting the ROI-inside image and the measured data as the ROI-outside measured data, and acquiring an ROI-outside image based on the ROI-outside measured data and estimating a difference between data acquired by re-projecting the ROI-outside image and the measured data as the ROI-inside measured data.

The measured data may be at least one of truncated data and data acquired at a low radiation dose of the X-ray transmitted by the X-ray source, wherein the low radiation dose is less than a reference value.

BRIEF DESCRIPTION OF THE DRAWINGS

These and/or other aspects will become apparent and more readily appreciated from the following description of the exemplary embodiments, taken in conjunction with the accompanying drawings in which:

FIGS. 6A, 6B, and 6C illustrate examples of truncations;

FIG. 14 illustrates an example of ROI-outside measured data and an ROI-outside image acquired according to an exemplary embodiment;

FIG. 20 is a flowchart of a method of a method of operating a medical imaging apparatus according to an exemplary embodiment;

FIG. 21 is a block diagram of a process in which a medical imaging apparatus acquires a reconstructed image from the measured data, according to an exemplary embodiment;

DETAILED DESCRIPTION

Figure 1:
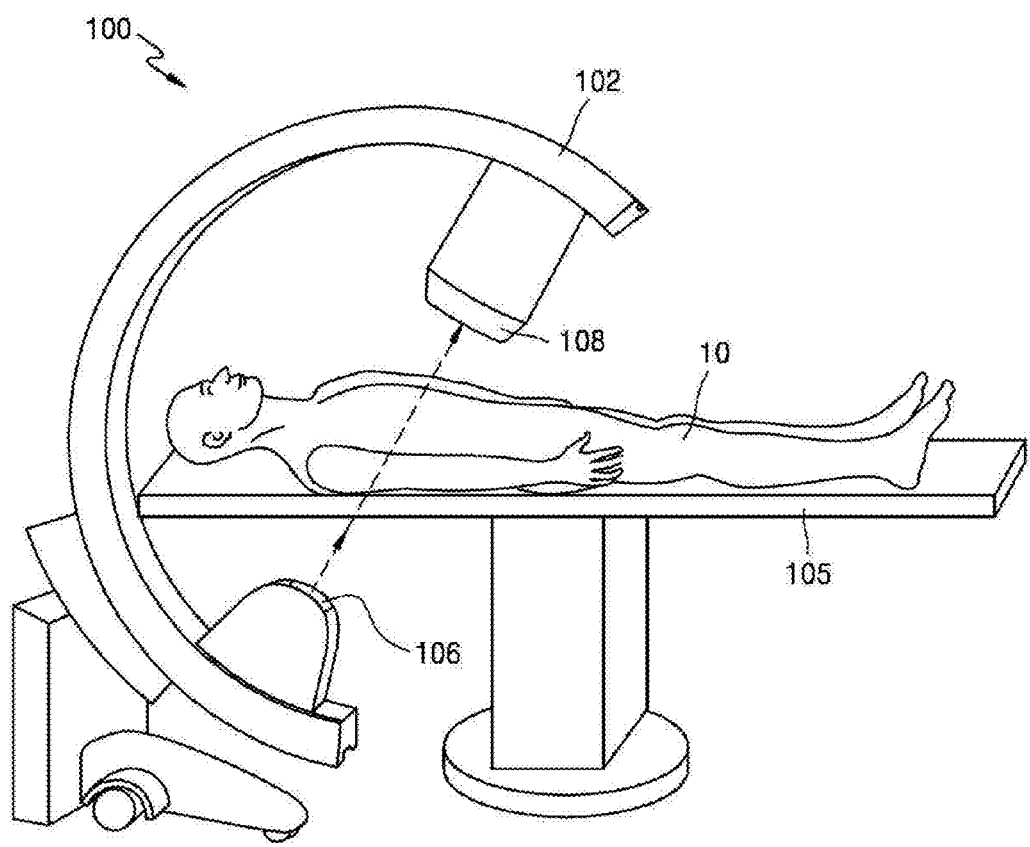
FIG. 1 illustrates an X-ray apparatus according to an exemplary embodiment.

Reference will now be made in detail to exemplary embodiments, examples of which are illustrated in the accompanying drawings, wherein like reference numerals refer to like elements throughout. As used herein, the term "and/or" includes any and all combinations of one or more of the associated listed items. Expressions such as "at least one of," when preceding a list of elements, modify the entire list of elements and do not modify the individual elements of the list.

Hereinafter, the present disclosure will be described more fully with reference to the accompanying drawings where exemplary embodiments of the disclosure are shown. However, this disclosure may be embodied in many different forms and should not be construed as being limited only to the exemplary embodiments set forth herein. Rather, these embodiments are provided so that this disclosure will be thorough and complete, and will fully convey the scope of the disclosure to one of ordinary skill in the art. Sizes of components in the drawings may be exaggerated for convenience of explanation. For example, since sizes and thicknesses of components in the drawings are illustrated for convenience of explanation, the embodiments of this disclosure are not limited by the drawings.

The terms used in the present disclosure have been selected from currently widely used general terms in consideration of the functions in the present disclosure. All terms including descriptive or technical terms used herein should be construed as having meanings that are obvious to one of ordinary skill in the art. When a term has an ambiguous meaning due to evolving of language, precedent cases, or appearance of new technologies, the meaning of a term used in this disclosure should first be clarified by its usage and/or definition in this disclosure. If the term cannot be clarified that way, then it should then be clarified as one of ordinary skill in the art would have understood the term at the time of this disclosure.

When a part "includes" or "comprises" an element, unless specified otherwise, it should be construed that the part can include at least one other element. Terms such as "~portion," "~unit," "~module," and "~block" in the disclosure may signify a unit to process at least one function or operation and the unit may be embodied by hardware such as a field-programmable gate array (FPGA) or an application-specific integrated circuit (ASIC), software, or a combination of hardware and software. However, the unit may be configured to be located in a storage unit medium to be addressed or configured to be able to operate one or more processors. Accordingly, the unit as an example includes constituent elements such as software constituent elements, object-oriented software constituent elements, class constituent elements, and task constituent elements, processes, functions, attributes, procedures, sub-routines, segments of program codes, drivers, firmware, microcodes, circuits, data, databases, data structures, tables, arrays, and variables. The constituent elements and functions provided by the "units" may be combined into a smaller number of constituent elements and units or may be further divided into additional constituent elements and units. Accordingly, the present disclosure is not limited by a specific combination of hardware and software.

In the present specification, an "image" may signify multi-dimensional data formed of discrete image elements, for example, pixels in a two-dimensional (2D) image and voxels in a three-dimensional (3D) image. For example, an image may include an X-ray, a computed tomography (CT) image, a magnetic resonance imaging (MRI) image, an ultrasound image, and a medical image of an object acquired by other medical imaging apparatuses.

Also, in the present specification, an "object" may include a human, an animal, or a part of a human or an animal. For example, an object may include body parts such as liver, heart, womb, brain, breast, abdomen, blood vessels, etc. Also, an object may include a phantom that signifies matter having a volume that is approximately the intensity and effective atomic number of a living thing, and may include a sphere phantom having a property similar to a human body.

Also, in the present specification, a "user" may be a doctor, a nurse, a clinical pathologist, a medical imaging expert, a technician who fixes a medical apparatus, etc., but the present disclosure is not limited thereto.

FIG. 1 illustrates an X-ray apparatus 100 according to an exemplary embodiment.

Referring to FIG. 1, the X-ray apparatus 100 may include a C-arm 102 having a C shape and may be able to continuously perform X-ray imaging for a predetermined time period. An X-ray source 106 may be provided at one end of the C-arm 102 and a detector 108 may be provided at the other end of the C-arm 102. The positions of the X-ray source 106 and the detector 108 on the C-arm 102 may be adjustable. Although it is not illustrated in FIG. 1, the C-arm 102 may be coupled to a ceiling, a floor, or both of the ceiling and the floor. Also, the X-ray apparatus 100 may further include a table 105 where an object 10 may be located.

The X-ray source 106 is configured to generate and transmit an X-ray. The detector 108 is configured to detect the X-ray that is transmitted by the X-ray source 106 through the object 10. A medical image may be acquired based on the X-ray detected by the detector 108. The C-arm 102 may rotate while the X-ray source 106 transmits X-ray. The detector 108 that rotates together with the X-ray source 106 may detect the X-ray that has transmitted through the object 10.

As a user adjusts a position of at least one of the C-arm 102 and the table 105, the object 10 may be imaged at various positions or various angles. For example, while a user rotates or moves the C-arm 102 and the table 105, the object 10 may be imaged to acquire medical images. Accordingly, the user may more efficiently image the object 10 using the X-ray apparatus 100 for a continuous time period, compared to a general fixed type X-ray apparatus.

The X-ray apparatus 100 may be used for fluoroscopy where a plurality of X-ray images or an X-ray motion picture is to be acquired for a continuous time period. For example, the X-ray apparatus 100 may be useful in medical treatments such as X-ray angiography or surgical operation. When a medical doctor needs to carefully examine a patient with vascular disease to diagnose a disease, the medical doctor continuously performs X-ray imaging during an examination time. Then, a state of blood vessels of a patient is examined through fluoroscopy, which uses X-rays to acquire real time moving images.

Accordingly, in a medical treatment such as angiography, X-ray is continuously transmitted toward the object 10 during treatment time to acquire fluoroscopic images. For example, X-ray imaging may allow a user, who may be a medical doctor, to see his progress when he is installing a guide wire around an object. Or, the X-ray imaging may allow the doctor to see where he is injecting a drug using a thin needle or a catheter.

During surgery, the doctor may insert a catheter, stent, or an injection needle into a human body. Accordingly, the user may perform the procedure by acquiring fluoroscopic images to check the position of a target object such as a catheter during the treatment. Accordingly, the user may be able to check whether the catheter is accurately inserted in a target position of the object 10.

The X-ray apparatus may be, for example, an interventional X-ray apparatus, interventional angiography C-arm X-ray apparatus, or a surgical C-arm X-ray apparatus.

Figure 2:
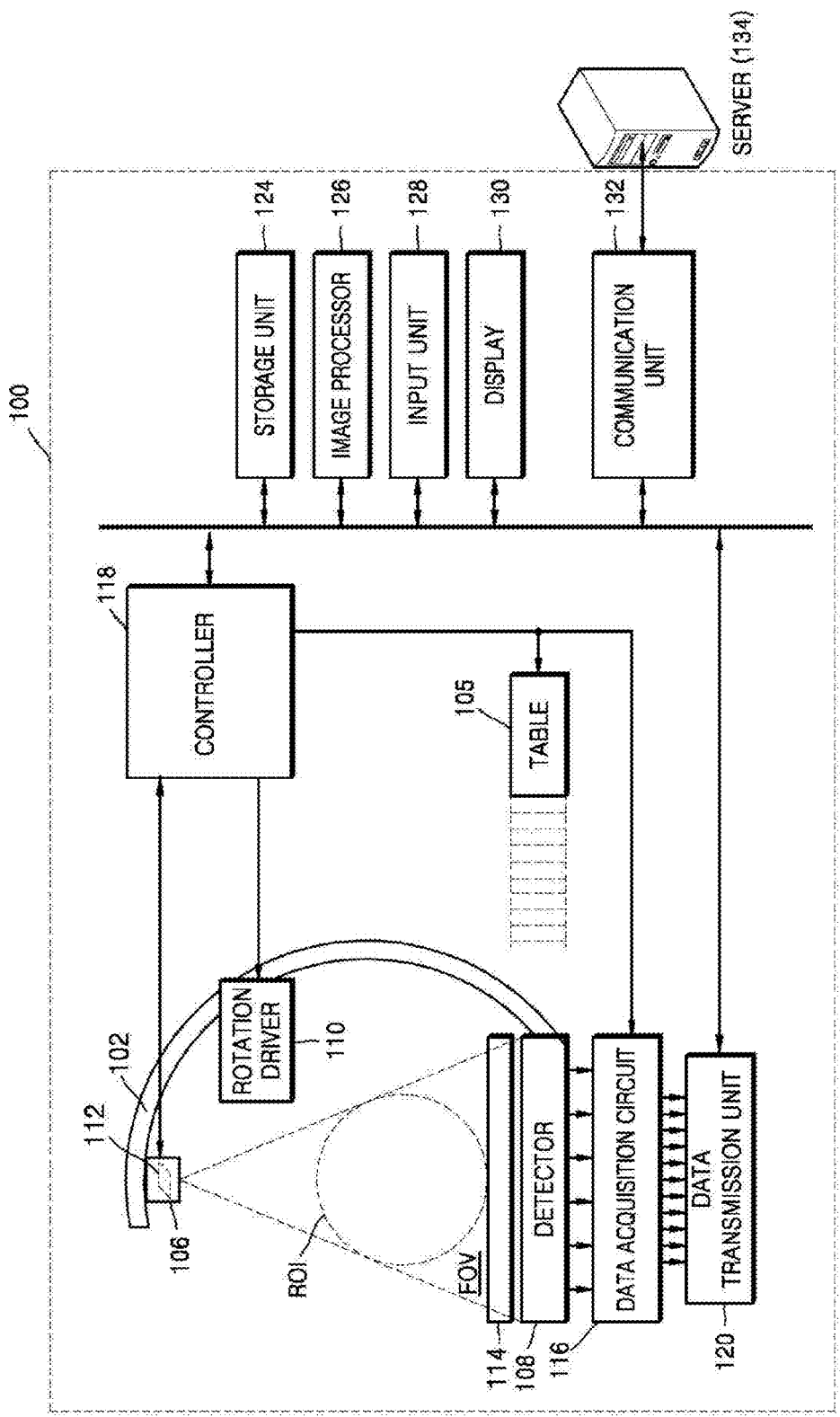
FIG. 2 illustrates a structure of the X-ray apparatus of FIG. 1.

FIG. 2 illustrates a structure of the X-ray apparatus 100 of FIG. 1.

Referring to FIG. 2, the X-ray apparatus 100 may include the X-ray source 106, the detector 108, and the C-arm 102 connecting the X-ray source 106 and the detector 108. Also, the X-ray apparatus 100 may further include a rotation driver 110, a data acquisition circuit 116, a data transmission unit 120, the table 105, a controller 118, a storage unit 124, an image processor 126, an input unit 128, a display 130, a communication unit 132.

The object 10 may be located on the table 105. The table 105 according to an exemplary embodiment may move in predetermined directions such as, for example, up, down, left, right, etc., and the motion of the table 105 may be controlled by the controller 118.

The X-ray source 106 and the detector 108 connected to the C-arm 102 to face each other have a predetermined field of view (FOV). When the X-ray source 106 and the detector 108 are rotated as the C-arm 102 rotates, the FOV may be changed accordingly.

X-ray radiation arriving at the detector 108 may include not only attenuated primary radiation forming a useful image, but also scattered radiation degrading the quality of an image. An anti-scatter grid 114 may be located on the detector 108 between a patient and the detector 108 (or a photosensitive film) in order to facilitate transmission of most of the primary radiation and attenuate the scattered radiation.

For example, the anti-scatter grid 114 may be configured in the form of alternately stacking strips of lead foil, a solid polymer material or solid polymer, and an interspace material such as a fiber composite material. However, the configuration of the anti-scatter grid 114 is not necessarily limited to this specific configuration.

The C-arm 102 may receive a drive signal and power from the rotation driver 110, and rotate the X-ray source 106 and the detector 108 at a predetermined rotation speed. The X-ray source 106 may generate and transmit an X-ray by receiving a voltage and current from a power distribution unit (PDU, not shown) through a high voltage generator (not shown). When the high voltage generator applies a predetermined tube voltage to the X-ray source 106, the X-ray source 106 may generate X-rays having a plurality of energy spectrums corresponding to the tube voltage. X-rays generated by the X-ray source 106 may be transmitted in a predetermined shape by a collimator 112.

The detector 108 may be located facing the X-ray source 106. The detector 108 may include a plurality of X-ray detection elements. A single X-ray detection element may form a single channel, but not limited thereto.

The detector 108 may detect the X-ray from the X-ray source 106 that is transmitted through the object 10 and generate an electrical signal corresponding to the intensity of the detected X-ray.

The detector 108 may include an indirect type detector that detects radiation by converting the radiation to light or a direct type detector that detect radiation by directly converting the radiation to electric charges. The indirect type detector may use a scintillator. The direct type detector may use a photon counting detector.

The data acquisition circuit 116 may be connected to the detector 108. The electrical signal generated by the detector 108 may be collected by the data acquisition circuit 116 wirelessly or via wire. Also, the electrical signal generated by the detector 108 may be provided to an analog-to-digital converter (not shown) through an amplifier (not shown) to form digital data.

Depending on the thickness and/or number of slices of the images, only part of digital data collected by the detector 108 may be provided to the image processor 126. Or the image processor 126 may select the data it may choose to use. The data transmission unit 120 may transmit the digital data to the image processor 126 wirelessly or via wire.

The controller 118 according to an exemplary embodiment may control operation of each of the modules in the X-ray apparatus 100. For example, the controller 118 may control operation of the table 105, the rotation driver 110, the collimator 112, the data acquisition circuit 116, the storage unit 124, the image processor 126, the input unit 128, the display 130, and the communication unit 132.

The image processor 126 may receive the digital data acquired from the data acquisition circuit 116, which may be, for example, raw data before processing, and perform pre-processing on the digital data.

The pre-processing may include, for example, a process of correcting irregular sensitivity between channels or a process of correcting signal loss due to radical decrease of signal intensity or an X-ray absorption material such as metal.

The pre-processed data by the image processor 126 may be referred to as projection data. The projection data may be stored in the storage unit 124 with its associated imaging parameters for data acquisition, for example, the tube voltage, imaging angle, etc.

The projection data may be a set of data values corresponding to the intensity of an X-ray transmitting through the object 10. For convenience of explanation, a set of the projection data simultaneously acquired at the same imaging angle with respect to all channels is referred to as a projection data set or measured data.

The storage unit 124 may include at least one type of storage unit media including flash memory, hard disk, multimedia card, card type memory such as SD or XD, random access memory (RAM), static RAM (SRAM), read-only memory (ROM), electrically erasable programmable ROM (EEPROM), programmable ROM (PROM), magnetic memory, magnetic disc, optical disc, etc.

Also, the image processor 126 may acquire a reconstructed image of the object 10 based on the measured data, where the reconstructed image may be three-dimensional (3D). The image processor 126 may generate a 3D image of the object 10 based on the acquired measured data using, for example, a cone beam reconstruction method.

The input unit 128 may receive an external input such as image processing conditions for X-ray tomography. For example, the X-ray tomography conditions may include setting a plurality of tube voltages and a plurality of energy values of X-rays, selecting an imaging protocol, selecting an image reconstruction method, setting an FOV area, setting an ROI area, setting the number of slices and slice thickness, and image post-processing parameters. Also the image processing conditions may include setting the resolution of an image, setting an attenuation coefficient of an image, and setting a combination ratio of an image.

The input unit 128 may include a device to receive input from the outside. For example, the input unit 128 may include a microphone, a keyboard, a mouse, a joystick, a touch pad, a touch pen, and a voice and gesture recognition device.

The display 130 may display an image reconstructed by the image processor 126.

The transmission and receiving of data or power between the above-described elements may be performed by using at least one of wired, wireless, and optical communication methods.

The communication unit 132 may communicate with an external device or an external medical apparatus via a server 134. Alternatively, the X-ray apparatus 100 may connect through the communication unit 132 to a workstation (not shown) that is configured to control the X-ray apparatus 100. This will be described with reference to FIG. 3.

Figure 3:
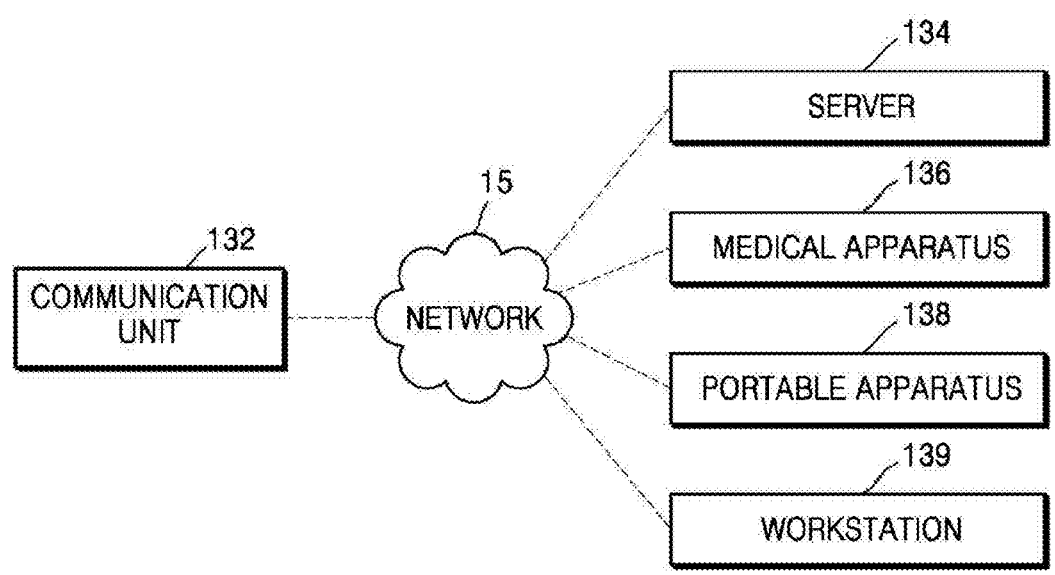
FIG. 3 is a block diagram of a structure of a communication unit of FIG. 2, according to an exemplary embodiment.

FIG. 3 is a block diagram of a structure of the communication unit 132 of FIG. 2, according to an exemplary embodiment.

The communication unit 132 may be connected to a network 15 wirelessly or via a wired connection and may communicate with an external device such as the server 134, a medical apparatus 136, a portable apparatus 138, or a workstation 139. The communication unit 132 may exchange data with a hospital sever or other medical apparatuses in a hospital through a medical image information system such as, for example, picture archiving and communication system (PACS).

Also, the communication unit 132 may perform data communication with the portable apparatus 138 using digital imaging and communications in medicine (DICOM), which is a medical digital imaging and communication standard.

The communication unit 132 may transmit and receive data related to the diagnosis of the object 10 via the network 15. Also, the communication unit 132 may transmit or receive a medical image acquired by the medical apparatus 136, which may be, for example, an MRI apparatus or an X-ray apparatus.

Furthermore, the communication unit 132 may receive information about a diagnosis history or treatment schedule of a patient from the server 134 and use the received information for clinical diagnosis of a patient. Also, the communication unit 132 may perform data communication not only with the server 134 or the medical apparatus 136 in a hospital, but also with the portable apparatus 138 of a user or a patient, and with the workstation 139.

Also, the communication unit 132 may transmit information about a status of equipment and a status of quality management to a system manager or a service manager via a network, and receive feedback thereon.

The workstation 139 may be in a separate area from the X-ray apparatus 100. For example, the X-ray apparatus 100 may be in a shield room and the workstation 139 may be in a console room. A shield room may be where the object 10 is imaged, and may also be variously referred to as the "imaging room," the "examination laboratory," or the "examination room." A user may control the X-ray apparatus 100 from a console room. The console room and the shield room may be separated from each other by a shielding wall to protect a user from a magnetic field, radiation, or a radio frequency (RF) signal transmitted from the shield room.

Figure 4:
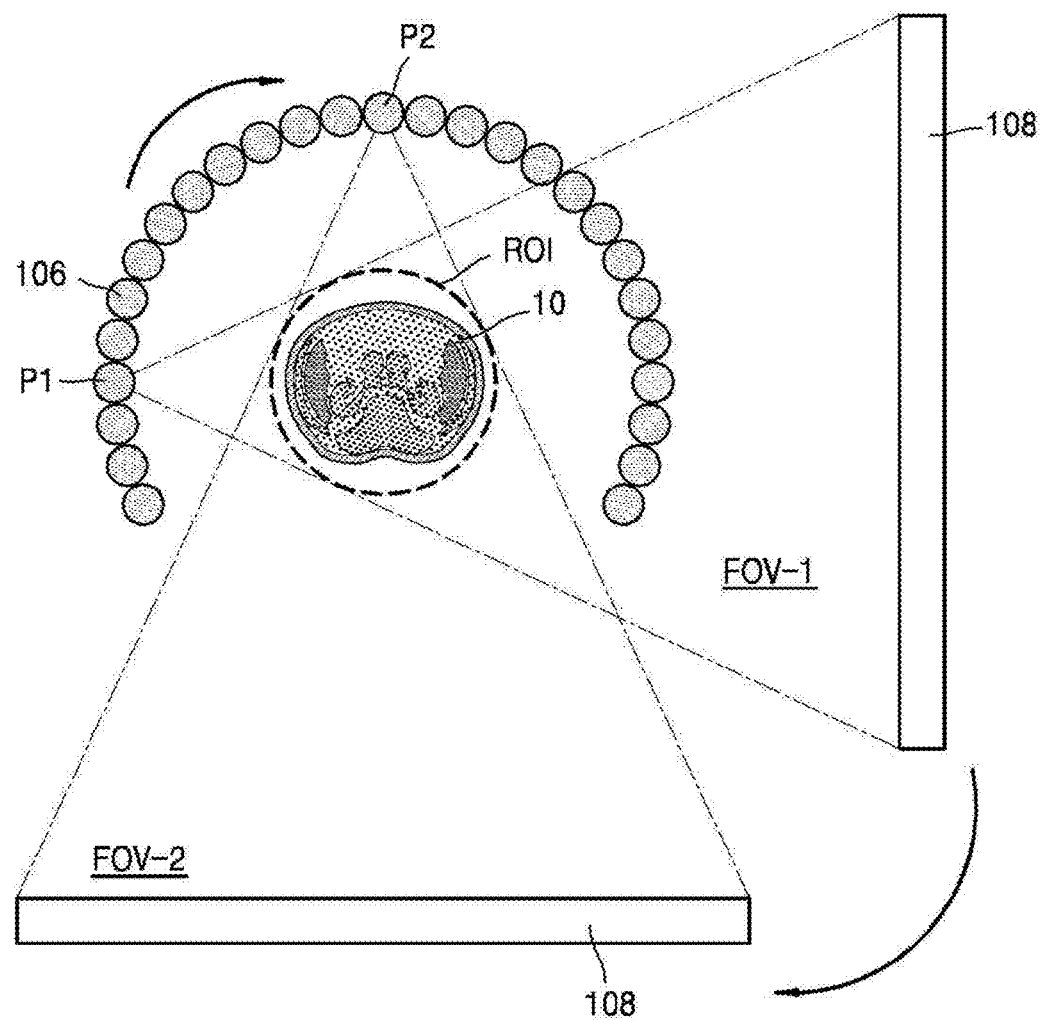
FIG. 4 illustrates an example of an operation in which the X-ray apparatus of FIG. 1 images an object, according to an exemplary embodiment.

FIG. 4 illustrates an example of an operation in which the X-ray apparatus 100 of FIG. 1 images the object 10, according to an exemplary embodiment. In FIG. 4, for convenience of explanation, only the X-ray source 106 and the detector 108 are illustrated among the elements of the X-ray apparatus 100 of FIG. 1.

Referring to FIGS. 1 and 4, the X-ray source 106 and the detector 108, connected to each other by the C-arm 102, may rotate around the object 10. The X-ray source 106 transmits an X-ray to the object 10, and the detector 108 detects the X-ray that passes through the object 10. The X-ray source 106 and the detector 108 arranged facing each other have a predetermined FOV. When the X-ray source 106 and the detector 108 rotate, the FOV may be changed accordingly. For example, when the X-ray source 106 is located at position P1, the detector 108 is located at a position facing the position P1 and has a field of view FOV-1 corresponding to the position P1. Also, when the X-ray source 106 is located at position P2, the detector 108 is located at a position facing the position P2 and has a field of view FOV-2 corresponding to the position P2.

The X-ray source 106 is moved by a predetermined rotation angle to change positions, for example, to P1 or P2, and transmits an X-ray. The detector 108 detects the X-ray transmitted at each position, for example, P1 or P2, of the X-ray source 106 to acquire projection data. The projection data may be a set of signal values corresponding to the intensity of the X-ray detected by the detector 108.

In detail, when the X-ray source 106 is located at position P1, the detector 108 may acquire first raw data by detecting the X-ray transmitted toward the object 10. Also, when the X-ray source 106 is located at position P2, the detector 108 may acquire second raw data by detecting the X-ray transmitted toward the object 10. Accordingly, the X-ray apparatus 100 may acquire a plurality of projection data corresponding to the raw data from the respective positions of the X-ray source 106. The X-ray apparatus 100 may acquire one measured data by combining a plurality of projection data. The measured data may be referred to as the sinogram. The X-ray apparatus 100 may acquire a reconstructed image by imaging a ROI from the measured data. The ROI is an area that may be reconstructed by the X-ray apparatus 100 to an image.

Figure 5:
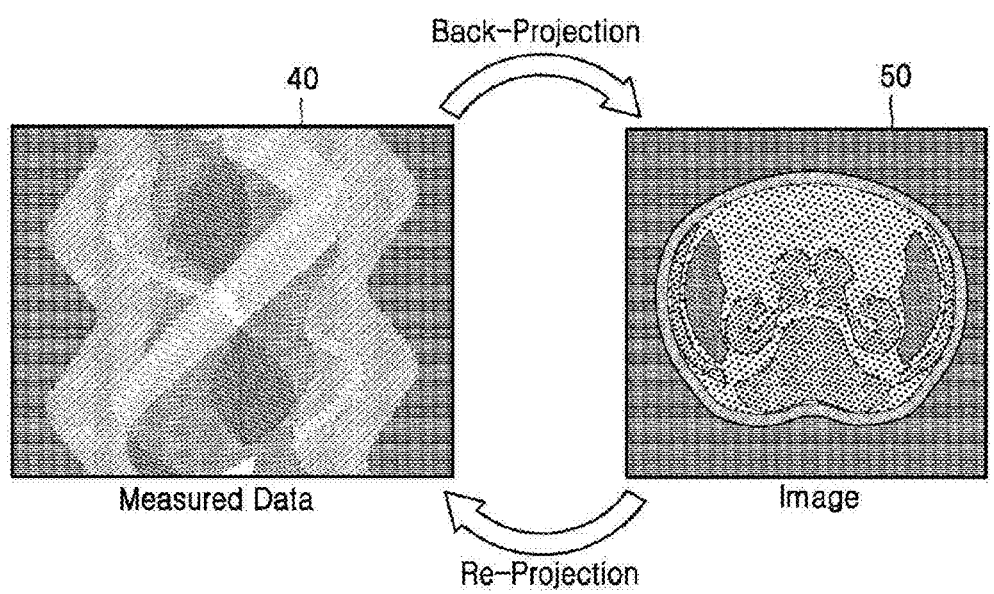
FIG. 5 illustrates a relationship between measured data and an image.

FIG. 5 illustrates a relationship between the measured data and an image.

Referring to FIG. 5, measured data 40 may be generated by combining a plurality of pieces of projection data acquired as the detector 108 detects the X-ray transmitted by the X-ray source 106 that rotates about the object 10, as illustrated in FIG. 4.

The image 50 may be acquired by back-projecting the measured data 40. Also, the measured data 40 may be acquired by re-projecting the image 50.

A technique to acquire the image 50 by back-projecting the measured data 40 is referred to as the analytical reconstruction technique. The analytical reconstruction technique may include a filtered back-projection (FBP) based reconstruction technique to acquire the image 50 by filtering and back-projecting the measured data 40, and a back-projection and filtration (BPF) technique to acquire the image 50 by back-projecting and filtering the measured data 40.

Referring back to FIG. 4, when the X-ray apparatus 100 of FIG. 1 images the object 10, that is, while the X-ray source 106 and the detector 108 rotate, the object 10 is within an FOV, for example, FOV-1 or FOV-2. However, while the X-ray source 106 and the detector 108 rotate, if a part of the object 10 is not within an FOV, truncation may be generated.

FIGS. 6A, 6B, and 6C illustrate examples of truncations. In FIG. 6, for convenience of explanation, only the X-ray source 106 and the detector 108 of the elements included in the X-ray apparatus 100 of FIG. 1 are illustrated.

Referring to FIGS. 6A, 6B, and 6C, when the size of the object 10 is too big (FIG. 6A), the size of the detector 108 is too small (FIG. 6B), or a distance DSO between the X-ray source 106 and the object 10 is too short, truncation may be generated. The truncation generated in the cases of FIGS. 6A, 6B, and 6C may cause an artifact in an image acquired from the measured data, thereby deteriorating the quality of the image. Accordingly, various embodiments of the present disclosure describe image reconstruction methods that may reduce artifact due to truncation during acquisition of an image.

In addition to the truncation, a low radiation dose may also deteriorate the quality of an image. According to an exemplary embodiment, the X-ray apparatus 100 of FIG. 1 performs X-ray imaging while the C-arm 102 rotates. Accordingly, as imaging time increases the total X-ray dosage transmitted to the object 10 increases as well. However, since X-ray is radiation that can be harmful to a human body, a user needs to minimize an X-ray dose the object 10 is exposed to during the X-ray imaging. Accordingly, the X-ray apparatus 100 according to an exemplary embodiment may image the object 10 with a low radiation dose.

Figure 7A:
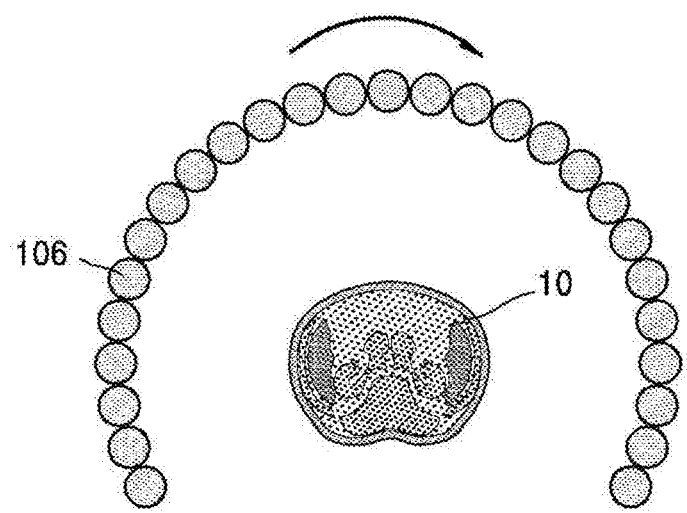
FIGS. 7A and 7B illustrate examples in which an X-ray apparatus according to an exemplary embodiment images an object with a high radiation dose or a low radiation dose.
Figure 7B:
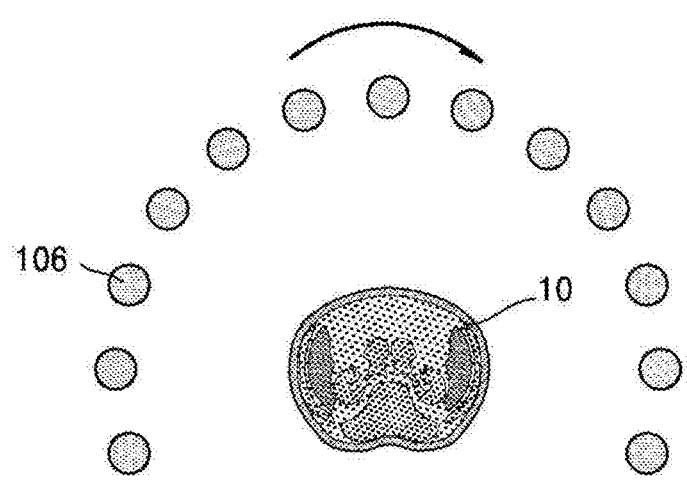

FIGS. 7A and 7B illustrate examples where the X-ray apparatus 100 according to an exemplary embodiment images the object 10 with a high radiation dose or a low radiation dose. In FIG. 7, for convenience of explanation, only the X-ray source 106 of the X-ray apparatus 100 of FIG. 1 is illustrated.

A rotation angle at which the position of the X-ray source 106 in FIG. 7A is changed is smaller than a rotation angle of the X-ray source 106 in FIG. 7B. Accordingly, in FIG. 7A, the X-ray apparatus 100 may image the object 10 with a higher total radiation dose compared to the case of FIG. 7B. For example, when the rotation angle of FIG. 7B is twice the rotation angle of FIG. 7A, the X-ray apparatus 100 of FIG. 7B may image the object 10 with a total X-ray dose that is 50% of that of FIG. 7A. Also, when the X-ray apparatus 100 of FIG. 7A images the object 10 by full sampling, the X-ray apparatus 100 of FIG. 7B is said to image the object 10 by undersampling.

Whether the total dose of X-rays transmitted by the X-ray apparatus 100 to image the object 10 is a high radiation dose or a low radiation dose may be determined by the rotation angle of the X-ray source 106. When the rotation angle of the X-ray source 106 is greater than a preset degree "n," the X-ray dose may be regarded as a low radiation dose. For example, the degree "n" may be 1°. In other words, when the X-ray source 106 transmits an X-ray to create an image by rotating at an angle greater than 1°, the X-ray dose may be regarded as a low radiation dose. However, this is merely exemplary and the rotation angle to determine whether the X-ray dose is a low radiation dose or not may be different according to the characteristics of the X-ray apparatus 100 such as the distance between the X-ray source 106 and the detector 108 of FIG. 1 or the size of the detector 108 of FIG. 1.

However, when the object 10 is imaged with a low radiation dose as in FIG. 7B, compared to the case of FIG. 7A, the number of projection data acquired by the X-ray apparatus 100 decreases. Accordingly, as incomplete measured data is acquired, a low radiation dose distortion phenomenon may occur that may lead to deteriorated quality of a reconstructed image.

Accordingly, when truncation is generated as in FIG. 6 or the X-ray apparatus 100 of FIG. 1 images the object 10 with a low radiation dose as in FIG. 7B, an image reconstruction method capable of preventing deterioration of image quality may be desired. In the following description, a medical imaging apparatus and a medical imaging method according to an exemplary embodiment that may address the issues of truncation and a low radiation dose are described.

Figure 8:
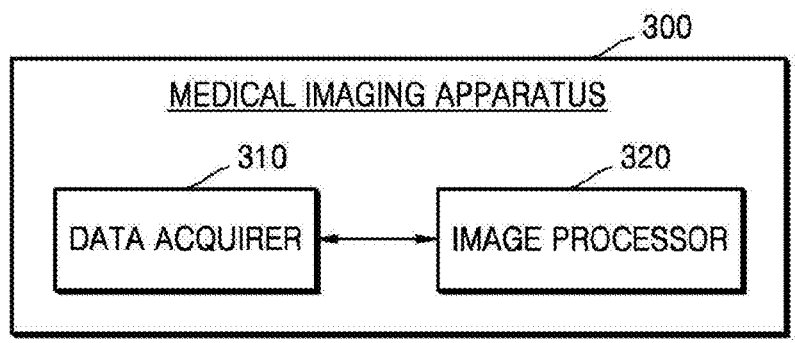
FIG. 8 is a block diagram of a structure of a medical imaging apparatus according to an exemplary embodiment.

FIG. 8 is a block diagram of a structure of a medical imaging apparatus 300 according to an exemplary embodiment. Referring to FIG. 8, the medical imaging apparatus 300 may include a data acquirer 310 and an image processor 320.

The data acquirer 310 may acquire measured data by performing X-ray imaging on an object. The measured data may be at least one of truncated data and data acquired with a low radiation dose smaller than a preset reference value. The measured data may be truncated data acquired under a truncation environment as illustrated in FIGS. 6A, 6B, and 6C. Alternatively, the measured data may be acquired by imaging the object with a low radiation dose as illustrated in FIG. 7B. As described in FIG. 7B, when the rotation angle of the X-ray source 106 is greater than a preset angle, the X-ray dose may be considered as a low radiation dose. The image processor 320 may generate a reconstruction image based on the measured data.

The medical imaging apparatus 300 may be included in the X-ray apparatus 100 of FIGS. 1 and 2. When the medical imaging apparatus 300 is included in the X-ray apparatus 100 of FIG. 2, the data acquirer 310 may correspond to at least one of the detector 108, the data acquisition circuit 116, and the data transmission unit 120. Also, the image processor 320 may correspond to the image processor 126 of FIG. 2. In this case, all the above specified elements may be included in the medical imaging apparatus 300 of FIG. 8.

Alternatively, the medical imaging apparatus 300 may be included in the server 134, the medical apparatus 136, the portable apparatus 138, or the workstation 139 of FIG. 3, which is connected to the X-ray apparatus 100 of FIG. 1 via a network. In this case, the data acquirer 310 of the medical imaging apparatus 300 may receive the measured data transmitted by the communication unit 132 of the X-ray apparatus 100 of FIG. 2 via the network 15 of FIG. 3.

A method in which the image processor 320 generates a reconstructed image, according to an exemplary embodiment, is described below.

Figure 9:
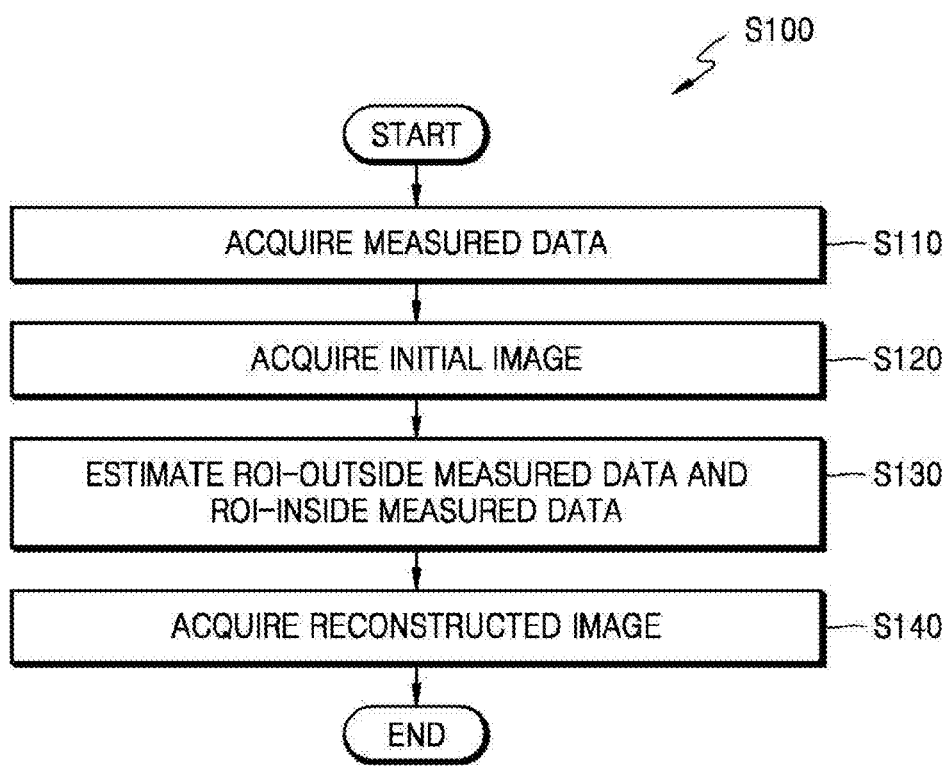
FIG. 9 is a flowchart of a method of operating a medical imaging apparatus according to an exemplary embodiment.

FIG. 9 is a flowchart of a method (S100) of operating a medical imaging apparatus according to an exemplary embodiment.

Referring to FIG. 9, the medical imaging apparatus may acquire measured data (S110). The medical imaging apparatus may acquire an initial image based on the measured data (S120). For example, an initial image may be the reconstructed image as described with reference to FIGS. 2, 4, 9, 10, 11, and 13-17. Additionally, an initial image may be formed by removing an outside of a ROI from a reconstructed image.

The medical imaging apparatus may alternately estimate ROI-outside measured data and ROI-inside measured data based on the measured data and the initial image (S130). The ROI-outside measured data may be an estimated difference between data acquired by re-projecting an inside of an ROI in the initial image and the measured data. The ROI-inside measured data may be an estimated difference between data acquired by re-projecting the ROI-outside image and the measured data.

In various embodiments of the present disclosure, either of the ROI-outside measured data or the ROI-inside measured data may be estimated first.

For example, the medical imaging apparatus may first estimate the ROI-outside measured data based on the measured data and the initial image. Next, the medical imaging apparatus may estimate the ROI-inside measured data based on a difference between the measured data and the ROI-outside measured data.

In another example, the medical imaging apparatus may first estimate ROI-inside measured data based on the measured data and the initial image. In this case, the medical imaging apparatus may estimate the ROI-outside measured data based on a difference between the measured data and the ROI-inside measured data. Next, the ROI-inside measured data may be updated based on the estimated ROI-outside measured data.

The medical imaging apparatus may acquire a reconstructed image based on the ROI-inside measured data (S140).

As such, the medical imaging apparatus according to an exemplary embodiment may acquire the ROI-inside measured data that is a result of removing influence of incomplete data about the outside of ROI from the measured data by removing the estimated ROI-outside measured data from the measured data. The reconstructed image acquired based on the ROI-inside measured data may have better image quality than the initial image acquired based on the measured data.

Figure 10:
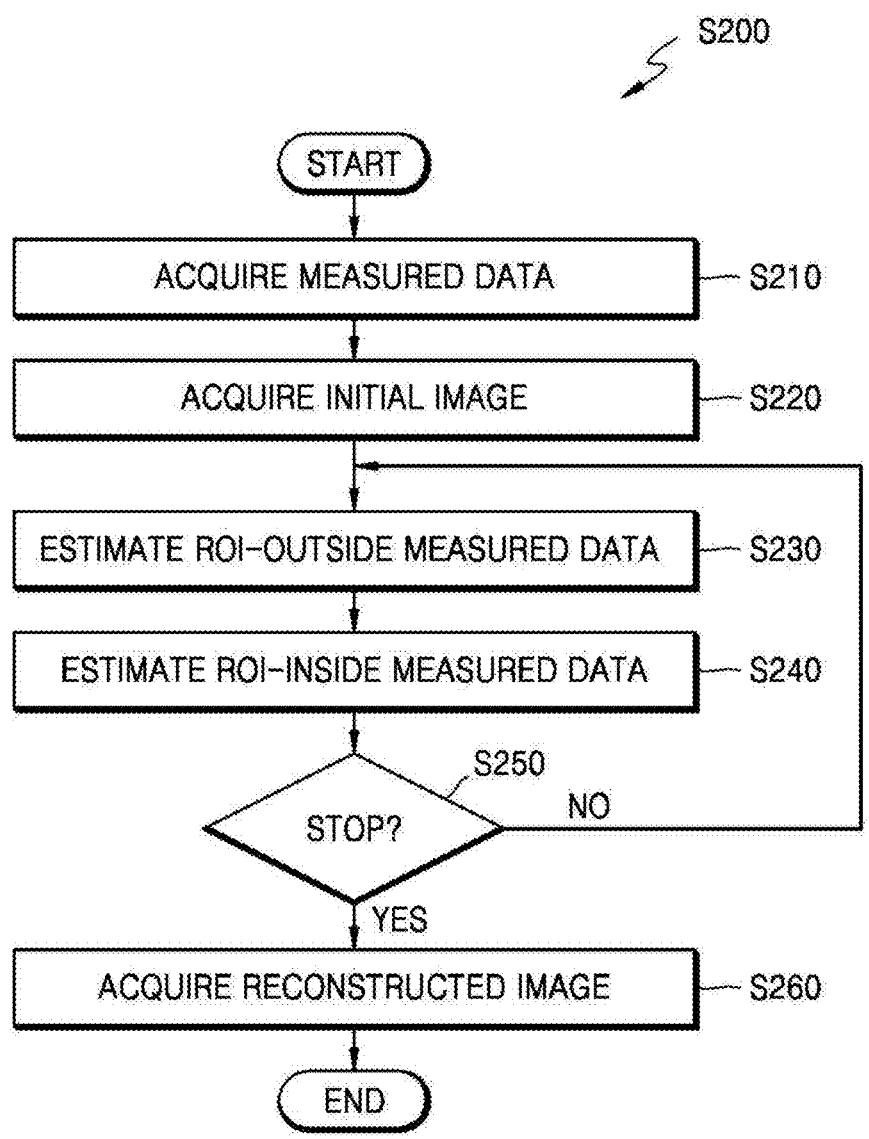
FIG. 10 is a flowchart of a method of operating a medical imaging apparatus according to another exemplary embodiment.

FIG. 10 is a flowchart of a method (S200) of operating a medical imaging apparatus according to another exemplary embodiment.

Referring to FIG. 10, the medical imaging apparatus may acquire measured data (S210). The medical imaging apparatus may acquire an initial image based on the measured data (S220).

The medical imaging apparatus may estimate ROI-outside measured data based on the measured data and the initial image (S230). The medical imaging apparatus may estimate ROI-inside measured data based on a difference between the measured data and the ROI-outside measured data (S240).

The medical imaging apparatus may determine whether to update the ROI-outside measured data and the ROI-inside measured data (S250). When it is determined to update, the medical imaging apparatus updates the estimated ROI-outside measured data and the estimated ROI-inside measured data by re-performing operations S230 and S240.

The medical imaging apparatus may perform an update operation including updating the ROI-outside measured data and the ROI-inside measured data by repeatedly performing operations S230, S240, and S250 until it is determined to stop updating in operation S250.

When the update operation is stopped, the medical imaging apparatus may acquire a reconstructed image based on a finally estimated ROI-inside measured data (S260). In other words, the medical imaging apparatus may acquire a reconstructed image based on a finally updated ROI-inside measured data.

A condition for determining whether to update may be set in various ways. For example, after repeating the operations S230 to S250 by a predetermined update repetition number, the update operation may be stopped. The repetition number may be initially determined as a default. Next, the repetition number may be adjusted by a user or determined based on the characteristics of the object or the characteristics of the measured data. However, the present disclosure is not limited thereto and other stopping conditions are described with reference to other drawings.

The methods S100 and S200 of operating a medical imaging apparatus of FIGS. 9 and 10 may be performed by the medical imaging apparatus 300 of FIG. 8. For example, the image processor 320 of the medical imaging apparatus 300 of FIG. 8 may perform the methods of S100 and S200. Alternatively, the methods S100 and S200 of operating a medical imaging apparatus of FIGS. 9 and 10 may be performed by the X-ray apparatus 100 of FIG. 2. For example, the image processor 126 of the X-ray apparatus 100 of FIG. 2 may perform the methods of S100 and S200. Alternatively, the methods S100 and S200 of operating a medical imaging apparatus may be performed by the server 134, the medical apparatus 136, the portable apparatus 138, or the workstation 139 of FIG. 3. Accordingly, all the above descriptions may be applied to the methods S100 and S200 of operating a medical imaging apparatus of FIGS. 9 and 10.

As such, according to an exemplary embodiment, ROI-outside measured data and ROI-inside measured data may be alternately estimated. The ROI-outside measured data and the ROI-inside measured data may be independently estimated. Also, accuracy of the estimated ROI-inside measured data may be improved by repeatedly performing alternate estimation of the ROI-outside measured data and the ROI-inside measured data. As the accuracy of the estimated ROI-inside measured data increases, the quality of a reconstructed ROI-inside image may increase as well.

Figure 11:
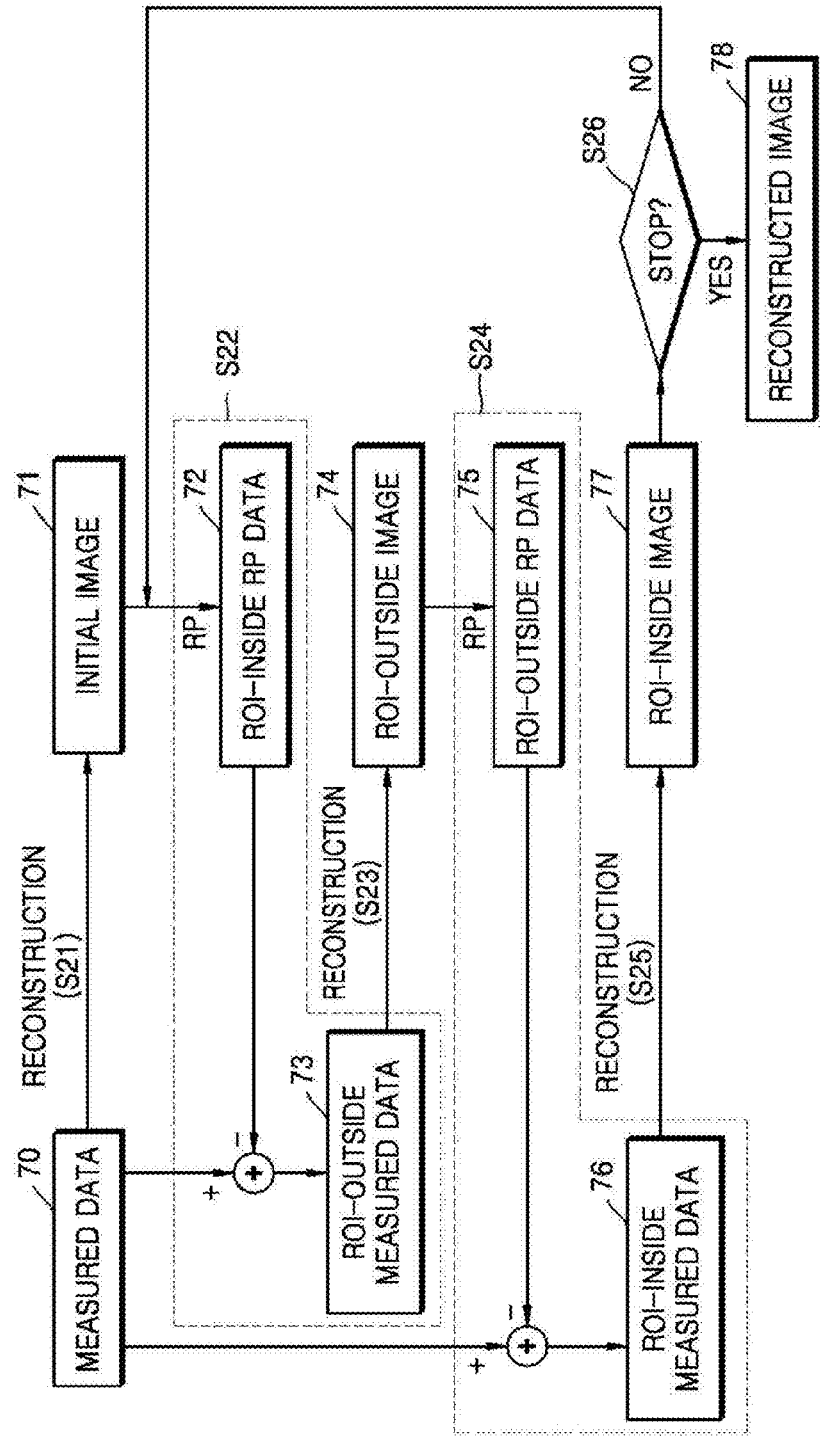
FIG. 11 is a block diagram of a process of acquiring a reconstructed image from data measured by a medical imaging apparatus, according to an exemplary embodiment.

FIG. 11 is a block diagram of a process of acquiring a reconstructed image from data measured by a medical imaging apparatus, according to an exemplary embodiment.

Referring to FIG. 11, a medical imaging apparatus may acquire an initial image 71 by reconstructing measured data 70 (S21). The medical imaging apparatus may acquire the initial image 71 by the analytical reconstruction technique described with reference to FIG. 5. Alternatively, the medical imaging apparatus may acquire the initial image 71 from the measured data 70 by an iterative reconstruction technique described with reference to FIG. 12. The iterative reconstruction technique may be a compressed sensing based iterative reconstruction technique. Also, when the initial image 71 is acquired by reconstructing the measured data 70, the medical imaging apparatus may apply extrapolation based truncation correction together with the reconstruction techniques.

The initial image 71 may be an image acquired by removing the outside of ROI from an image acquired by reconstructing the measured data 70 (S21), leaving the inside of the ROI only. For example, in the image acquired by reconstructing the measured data 70 (S21), by processing pixel values of pixels included in the outside of the ROI as "0," the initial image 71 where the outside of the ROI is removed may be acquired.

The medical imaging apparatus may re-project (RP) the inside of the ROI in the initial image 71 to acquire ROI-inside RP data 72. The medical imaging apparatus may acquire the ROI-inside RP data 72 by re-projecting only the inside of the ROI in the initial image 71. When the initial image 71 is an image where the outside of ROI is removed, the medical imaging apparatus may acquire the ROI-inside RP data 72 by re-projecting the initial image 71. The re-projecting may be performed in various ways, for example, ray-driven, voxel-driven, or distance-driven.

The medical imaging apparatus may estimate a difference between the measured data 70 and the ROI-inside RP data 72 that is data acquired by re-projecting the inside of ROI in the initial image 71, as ROI-outside measured data 73 (S22). The measured data 70 may include both of data about the inside of ROI and data about the outside of ROI. However, since the ROI-inside RP data 72 is data acquired by re-projecting the inside of ROI of the initial image 71, the ROI-outside measured data 73 acquired by removing the ROI-inside RP data 72 from the measured data 70 may be estimated as data about the outside of ROI of the measured data 70.

The medical imaging apparatus may acquire an ROI-outside image 74 by reconstructing the estimated ROI-outside measured data 73 (S23). The medical imaging apparatus may acquire the ROI-outside image 74 based on the ROI-outside measured data 73 using the iterative reconstruction technique. The medical imaging apparatus may acquire the ROI-outside image 74 by removing the inside of ROI from an image acquired based on the ROI-outside measured data 73 using the iterative reconstruction technique, leaving the outside of ROI only.

The medical imaging apparatus may acquire ROI-outside RP data 75 by re-projecting the ROI-outside image 74. The medical imaging apparatus may estimate ROI-inside measured data 76 as a difference between the ROI-outside RP data 75 and the measured data 70 (S24).

The medical imaging apparatus may acquire ROI-inside image 77 by reconstructing the estimated ROI-inside measured data 76 (S25). The medical imaging apparatus may acquire the ROI-inside image 77 based on the ROI-inside measured data 76 using the iterative reconstruction technique. The medical imaging apparatus may acquire the ROI-inside image 77 by removing the outside of ROI from an image acquired based on the ROI-inside measured data 76 using the iterative reconstruction technique, leaving the inside of ROI only.

The medical imaging apparatus may determine whether to update the ROI-outside measured data 73 and the ROI-inside measured data 76 (S26).

When it is determined to update further, the medical imaging apparatus updates the ROI-outside measured data 73 based on the ROI-inside image 77, not the initial image 71. Hence, the ROI-inside measured data 76 is updated based on the updated ROI-outside measured data 73, and the ROI-inside image 77 is updated based on the updated ROI-inside measured data 76.

In detail, the updated ROI-inside RP data 72 may be acquired by re-projecting the inside of the ROI in the ROI-inside image 77. There may be a difference between the ROI-inside RP data 72 acquired by re-projecting the initial image 71 before update and the ROI-inside RP data 72 acquired by re-projecting the ROI-inside image 77. The medical imaging apparatus may update the ROI-outside measured data by re-estimating the difference between the ROI-inside RP data 72 acquired by re-projecting the inside of ROI in the ROI-inside image 77 and the measured data 70 as the ROI-outside measured data (re-performing operation S22).

The medical imaging apparatus may acquire the updated ROI-outside image 74 by reconstructing the updated ROI-outside measured data 73 (re-performing operation S23). The medical imaging apparatus may update the ROI-inside measured data 76 by re-estimating a difference between the ROI-outside RP data 75, acquired by re-projecting the updated ROI-outside image 74, and the measured data 70 as the ROI-inside measured data 76 (re-performing operation S24).

The medical imaging apparatus may acquire the updated ROI-inside image 77 by reconstructing the updated ROI-inside measured data 76 (re-performing operation S25). The medical imaging apparatus may determine again whether to update (re-performing operation S26).

As such, the medical imaging apparatus may iteratively perform the operations S22, S23, S24, S25, and S26 until a determination is made to stop updating in operation S26. Thus, the update operations including updating the ROI-outside measured data 73, updating the ROI-inside measured data 76, and updating the ROI-inside image 77 may be iteratively performed.

When it is determined to stop updating in operation S26, the medical imaging apparatus may acquire a reconstructed image 78 based on the finally updated ROI-inside image 77. The reconstructed image 78 may be the finally updated ROI-inside image 77.

Conditions for determining whether to update may be set in various ways. For example, the update operation may be stopped after a predetermined number of updates. For example, the predetermined update repetition number may be two or more. However, the present disclosure is not limited thereto. Alternatively, the update operation may be stopped when a difference between the updated ROI-inside measured data 76 and the update acquired by re-projecting the ROI-inside image 77 is equal to or less than a predetermined threshold value. The threshold value may be initially determined to be a default. The threshold value may also be adjusted by a user or determined based on the characteristics of the object or the characteristics of the measured data. However, the present disclosure is not limited thereto. For example, the threshold value may be set to an attenuation value having 6 decimal places (0.00000×). However, the present disclosure is not limited thereto.

Also, the user may determine whether to update after checking the ROI-inside image 77.

Figure 12:
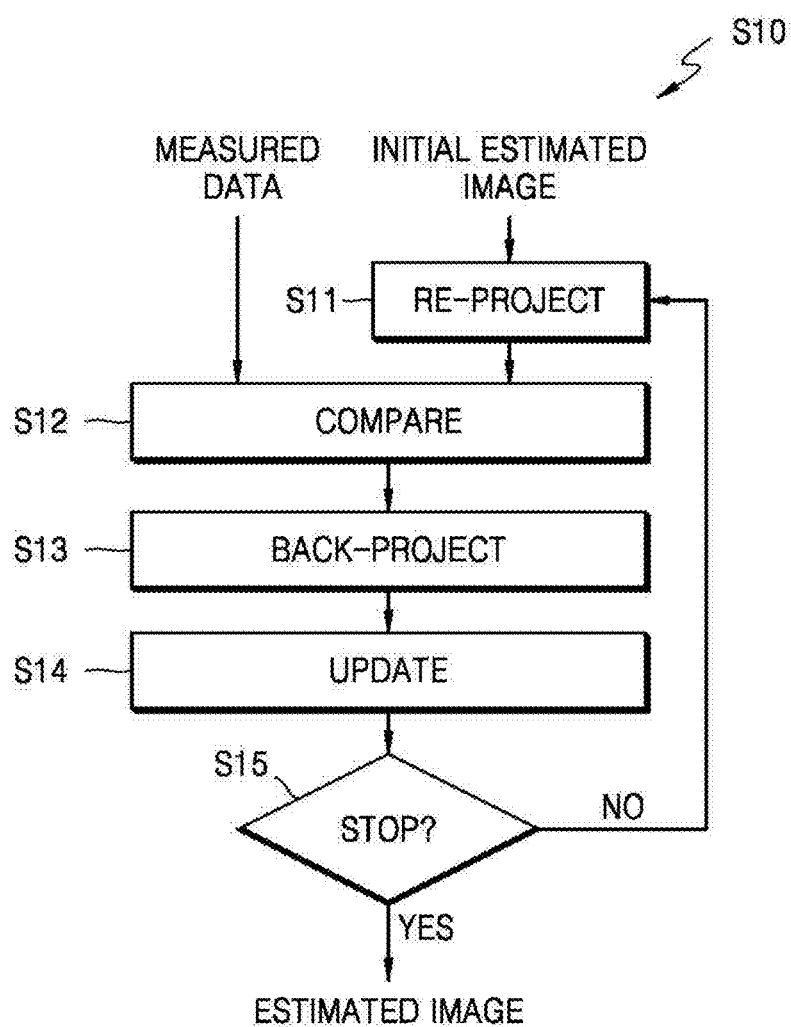
FIG. 12 is a flowchart of a process in which a medical imaging apparatus according to an exemplary embodiment acquires an estimated image through iterative reconstruction from measured data.

FIG. 12 is a flowchart of a process S10 in which a medical imaging apparatus according to an exemplary embodiment acquires an estimated image through iterative reconstruction from measured data.

The process S10 of FIG. 12 may be applied to operation S21 of reconstructing the initial image 71 from the measured data 70 of FIG. 11, operation S23 reconstructing the ROI-outside image 74 from the ROI-outside measured data 73, and operation S25 of reconstructing the ROI-inside image 77 from the ROI-inside measured data 76. In other words, the measured data of FIG. 12 may be the measured data 70, the ROI-outside measured data 73, or the ROI-inside measured data 76 in FIG. 11. The estimated image of FIG. 12 may be the initial image 71, the ROI-outside image 74, or the ROI-inside image 77 according to the type of the measured data.

Referring to FIG. 12, the medical imaging apparatus may re-project an initial estimated image (S11). The initial estimated image may be a default image. The initial estimated image may be an image in which all pixel values are constant. For example, the initial estimated image may be an image in which all pixel values are "0."

The medical imaging apparatus may compare the data acquired by re-projecting the initial estimated image and the measured data, and acquire a difference value therebetween (S12). The medical imaging apparatus may back-project the difference value (S13). The medical imaging apparatus may acquire an updated estimated image by overlapping an image acquired by re-projecting the difference value on the initial estimated image (S14).

The medical imaging apparatus may determine whether to stop the iterative reconstruction process (S15). For example, when the difference value acquired in the operation S12 is equal to or less than a predetermined threshold value, the iterative reconstruction process may be stopped. For example, the threshold value may be set to an attenuation value having 6 decimal places (0.00000×). However, the present disclosure is not limited thereto and the threshold value may be set in various ways according to the quality of an image that the user wants or the characteristics of the object.

Unless the iterative reconstruction process is stopped, the medical imaging apparatus re-performs re-projecting the estimated image updated in the operation S14 (S11), acquiring a difference value by comparing the data acquired by re-projecting the updated estimated image and the measured data (S12), back-projecting the difference value (S13), and updating again the estimated image by overlapping the image acquired by back-projecting the difference on the updated estimated image (S14). Next, the medical imaging apparatus may determine again whether to stop the iterative reconstruction process (S15).

When the iterative reconstruction process is stopped, the medical imaging apparatus may determine the finally updated estimated image to be an estimated image. The medical imaging apparatus may further perform post-filtering such as TV minimization or soft thresholding on the estimated image.

Figure 13:
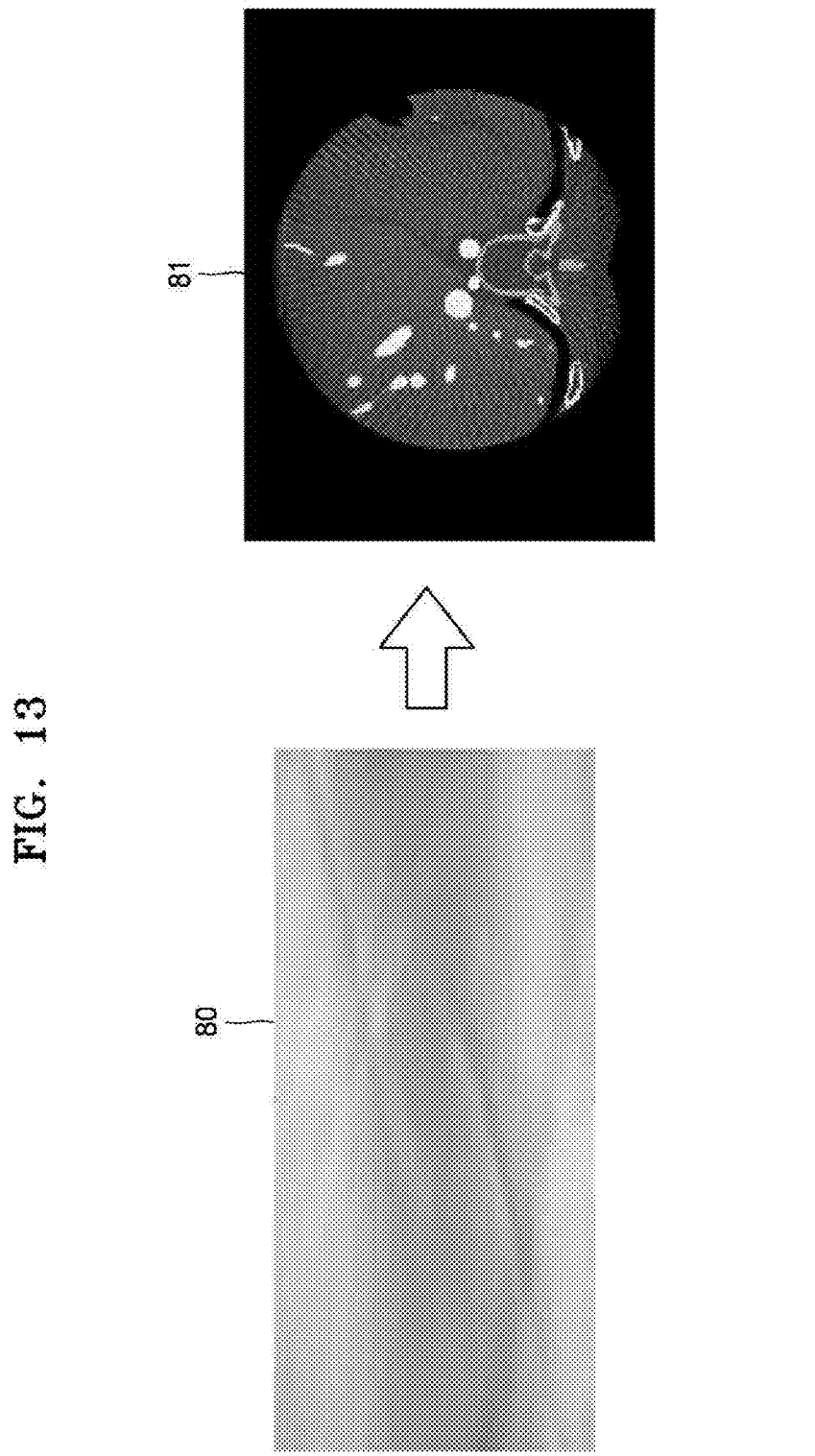
FIG. 13 illustrates an example of measured data and an initial image acquired according to an exemplary embodiment.
Figure 15:
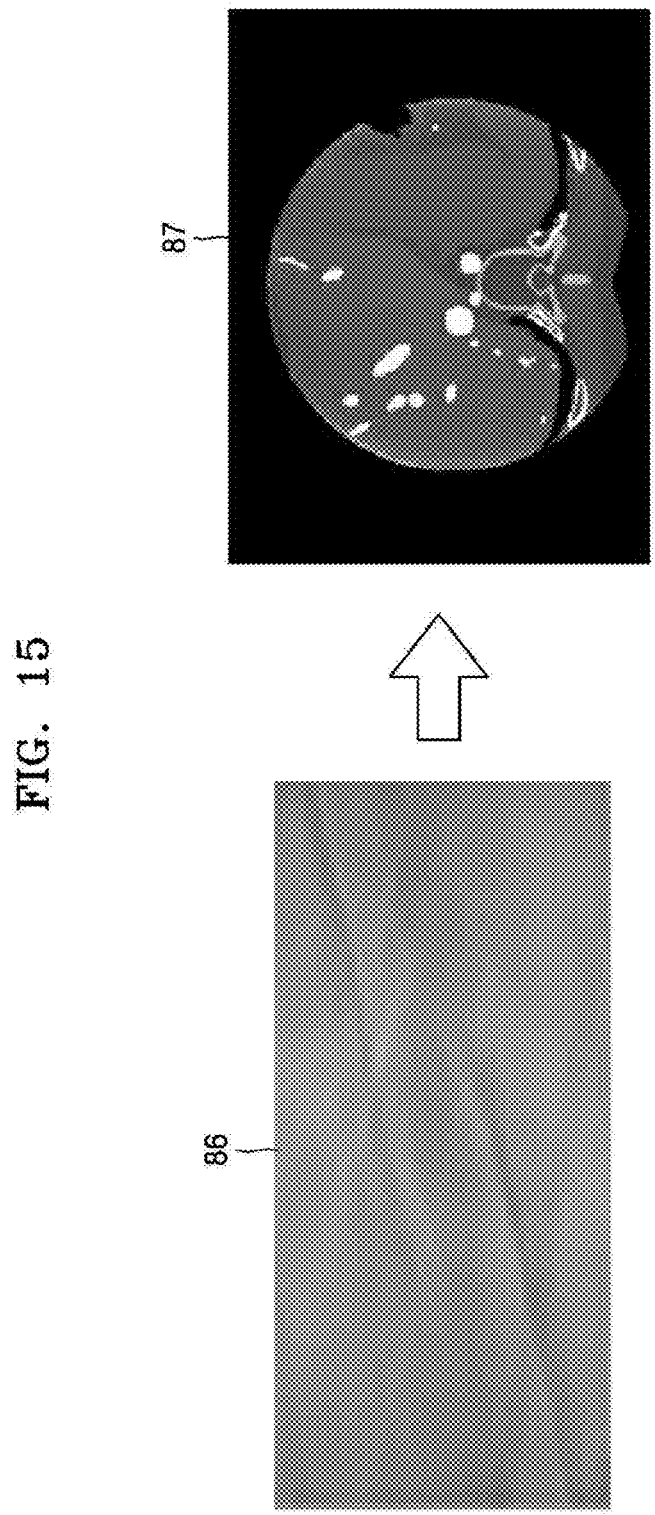
FIG. 15 illustrates an example of ROI-inside measured data and an ROI-inside image acquired according to an exemplary embodiment.

Next, referring to FIGS. 13 to 15, according to an exemplary embodiment, the data and image acquired from a process of acquiring a reconstructed image from the measured data.

FIG. 13 illustrates an example of measured data 80 and an initial image 81 acquired according to an exemplary embodiment.

Referring to FIG. 13, the medical imaging apparatus may acquire the initial image 81 by reconstructing the measured data 80. The measured data 80 is an example of the measured data 70 of FIG. 11 and the initial image 81 is an example of the initial image 71 of FIG. 11.

It may be seen that the quality of the initial image 81 has many artifacts and is not good. The quality of the initial image 81 may be deteriorated due to truncation or a low radiation dose.

FIG. 14 illustrates an example of ROI-outside measured data 83 and an ROI-outside image 84 acquired according to an exemplary embodiment.

Referring to FIG. 14, the medical imaging apparatus may acquire the ROI-outside image 84 by reconstructing the ROI-outside measured data 83. The ROI-outside measured data 83 is an example of the ROI-outside measured data 73 of FIG. 11, and the ROI-outside image 84 is an example of the ROI-outside image 74 of FIG. 11.

FIG. 15 illustrates an example of ROI-inside measured data 86 and an ROI-inside image 87 acquired according to an exemplary embodiment.

Referring to FIG. 15, the medical imaging apparatus may acquire the ROI-inside image 87 by reconstructing the ROI-inside measured data 86. The ROI-inside measured data 86 is an example of the ROI-inside measured data 76 of FIG. 11, and the ROI-inside image 87 is an example of the ROI-inside image 77 of FIG. 11.

In comparison with FIG. 13 and FIG. 15, compared to the initial image 81 of FIG. 13 acquired by reconstructing the measured data 80, the ROI-inside image 87 reconstructed based on the ROI-inside measured data 86 may have improved image quality as artifact is removed.

Figure 16:
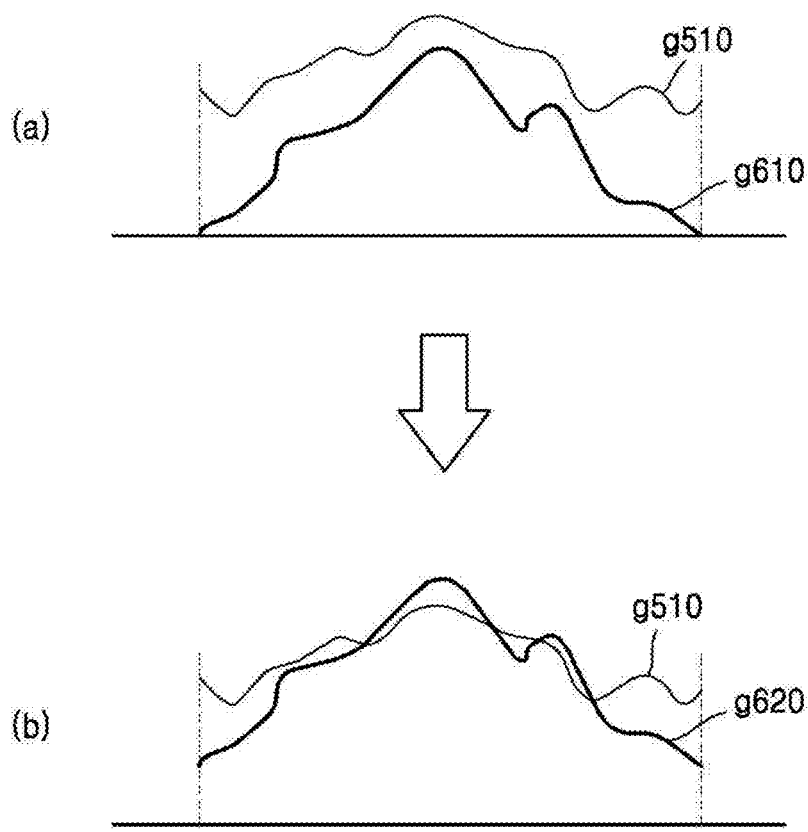
FIG. 16 illustrates a case of acquiring a reconstructed image from measured data by an iterative reconstruction technique according to an exemplary embodiment.

FIG. 16 illustrates a case of acquiring a reconstructed image from the measured data by an iterative reconstruction technique according to an exemplary embodiment.

In graph (a) of FIG. 16, the horizontal axis corresponds to the position of the detector 108 of FIG. 4 and the vertical axis corresponds to the magnitude of data. The line g510 is measured data and the line g610 is data acquired by re-projecting an initial estimated image. As described in FIG. 12, as the initial estimated image may be iteratively updated so that the difference between the measured data (g510) and the re-projected data (g610) of the initial estimated image is minimized, thereby acquiring the estimated image. In FIG. 16, the estimated image that is iteratively updated may be a reconstructed image.

Graph (b) of FIG. 16 illustrates a comparison between the measured data (g510) and the re-projected data (g620) of the reconstructed image. The difference between the re-projected data (g620) of the reconstructed image acquired through iterative update and the measured data (g510) may be greatly reduced, compared to the graph (a) of FIG. 16.

However, the re-projected data (g620) of the reconstructed image is greater than the measured data (g510) at a central portion of the detector but smaller than the measured data (g510) at the edges of the detector. Such a non-linear offset is generated when the measured data is acquired in a truncation situation or by low-radiation dose imaging. When truncation is generated, the measured data includes data about both the inside of ROI and outside of ROI. In other words, since the iterative reconstruction does not consider or treat data about the outside of ROI, the non-linear offset may not be removed through the iterative reconstruction. Accordingly, the quality of a reconstructed image may be deteriorated and acquiring a high quality reconstructed image may be impossible.

Figure 17:
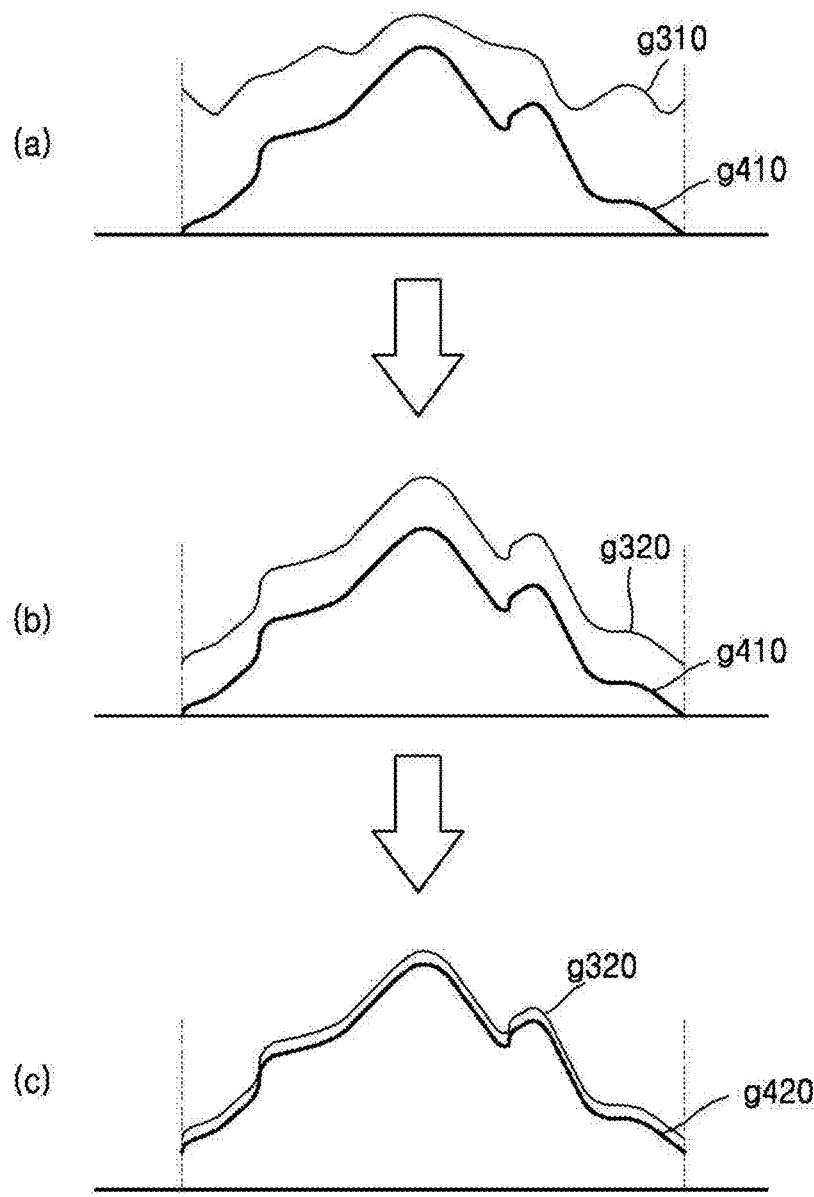
FIG. 17 illustrates a process of acquiring a reconstructed image from the measured data, according to an exemplary embodiment.

FIG. 17 illustrates a process of acquiring a reconstructed image from the measured data, according to an exemplary embodiment.

In graph (a) of FIG. 17, the line g310 denotes measured data, and the line g410 denotes data acquired by re-projecting an initial image. According to an exemplary embodiment, the medical imaging apparatus may estimate ROI-outside measured data through a difference between the data acquired by re-projecting the initial image (g410) and the measured data (g310). Also, the ROI-inside measured data may be estimated based on the ROI-outside measured data.

In graph (b) of FIG. 17, the line g320 denotes the ROI-inside measured data. In other words, the ROI-inside measured data (g320) acquired by removing the ROI-outside measured data from the measured data (g310) may be estimated. Next, a reconstructed image may be acquired from the ROI-inside measured data (g320) through the iterative reconstruction technique. A reconstructed image may be acquired through the iterative reconstruction technique based on the ROI-inside measured data (g320) and the initial image.

In graph (c) of FIG. 17, the line g420 denotes re-projected data of the reconstructed image. When the ROI-inside measured data (g320) and the re-projected data (g420) of the reconstructed image are compared, it may be seen that the two pieces of data are almost matched with each other and non-linear offset is not generated, unlike graph (b) of FIG. 16.

As such, according to an exemplary embodiment, the ROI-inside measured data acquired by removing the effect of incomplete data about the outside of ROI from the measured data may be estimated, and the reconstructed image may be acquired from the ROI-inside measured data through the iterative reconstruction. In this case, the non-linear offset, which may be present in the reconstructed image acquired from the measured data, may be alleviated by iterative reconstruction and, thus, the quality of a reconstructed image may be improved. Also, according to an exemplary embodiment, a high quality image may be provided even when the object is imaged at a low radiation dose. Accordingly, the medical imaging apparatus that has high safety with respect to the object and has an improved user satisfaction may be provided.

Figure 18A:
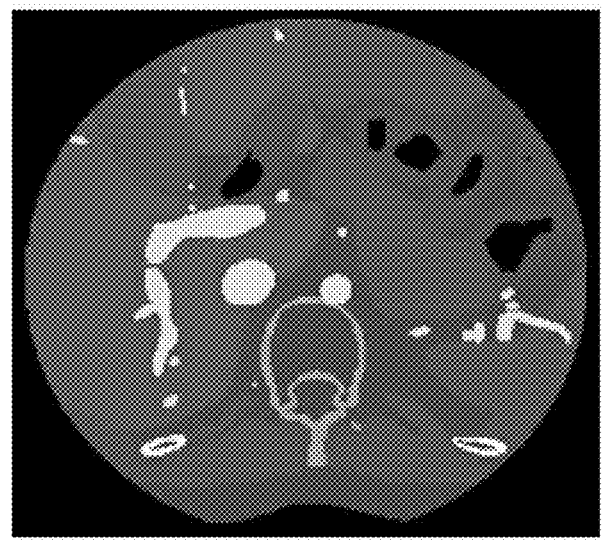
FIGS. 18A to 18D are examples of the reconstructed images.
Figure 18B:
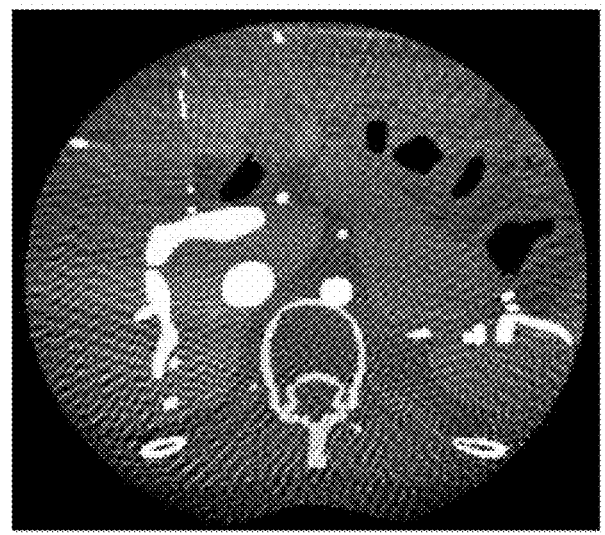
Figure 18C:
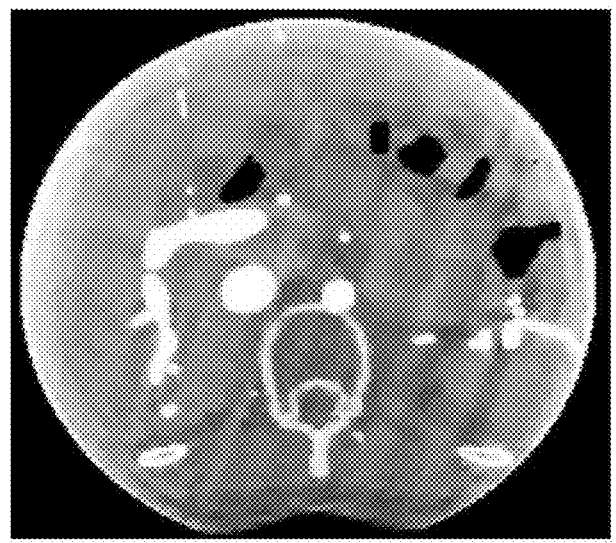
Figure 18D:
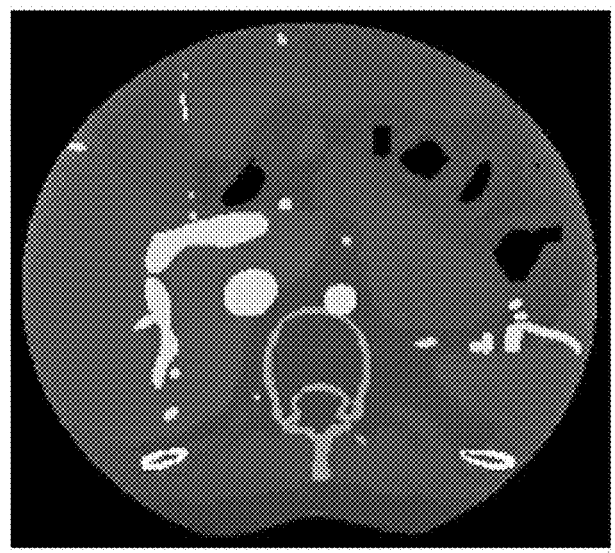

FIGS. 18A to 18D are examples of the reconstructed images. FIG. 18A is a ground truth image that is a reference for evaluating the quality of an image. FIGS. 18B, 18C, and 18D are images all acquired from the measured data acquired by imaging an object at a radiation dose of 50%. FIG. 18B is a reconstructed image acquired from the measured data through the analytical reconstruction technique. FIG. 18C is a reconstructed image acquired from the measured data through the iterative reconstruction technique. FIG. 18D is a reconstructed image acquired from the measured data according to an exemplary embodiment. Among FIGS. 18B, 18C, and 18D, the image of FIG. 18D is closest to the ground truth image of FIG. 18A. Also, it may be seen that artifacts due to truncation appearing on the image of FIG. 18B are not shown in the image of FIG. 18D. In other words, it may be seen from the image of FIG. 18D that a low radiation dose distortion phenomenon may be improved and artifacts removed from a boundary of the inside and outside of ROI, that is, an adjacent area of truncation. As such, it may be seen from FIGS. 18A to 18D that the quality of the reconstructed images acquired according to an exemplary embodiment is remarkably improved compared to a case that does not follow the present exemplary embodiment.

Figure 19A:
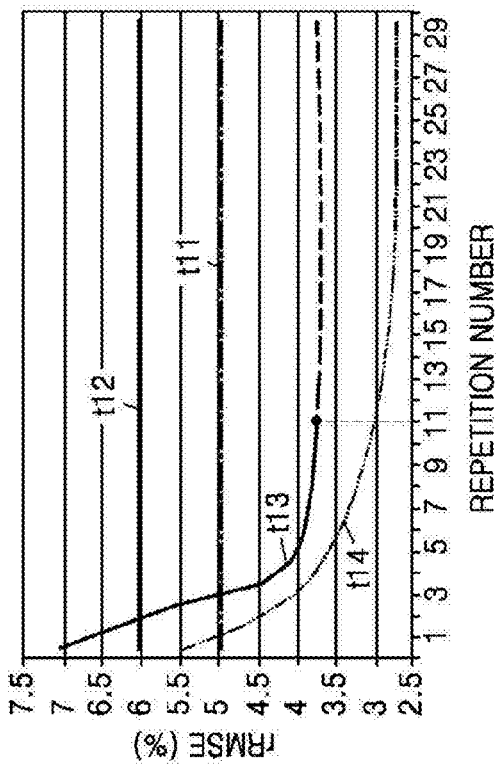
FIGS. 19A and 19B are graphs showing the quality of reconstructed images variously acquired from truncated measured data.
Figure 19B:
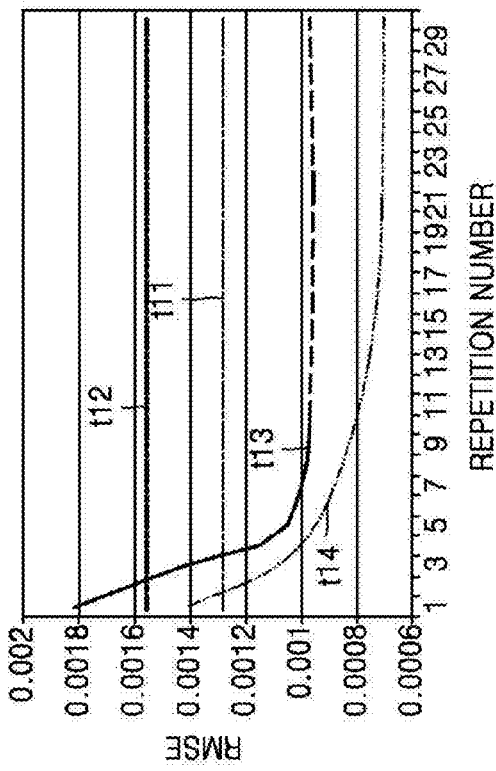

FIGS. 19A and 19B are graphs showing the quality of reconstructed images variously acquired from truncated measured data. FIG. 19A illustrates a root mean square error (RMSE) with respect to a repetition number, and FIG. 19B illustrates a relative RMSE (rRMSE) with respect to the repetition number. In FIG. 19A, RMSE denotes linear attenuation ($mm^{-1}$), and the unit of rRMSE in FIG. 19B is percentage (%).

Referring to FIGS. 19A and 19B, line t11 denotes RMSE and rRMSE when the measured data acquired by imaging the object at a radiation dose of 100% using an analytical reconstruction technique. Line t12 denotes RMSE and rRMSE when the measured data acquired by imaging the object at a radiation dose of 50% using the analytical reconstruction technique.

Lines t13 and t14 indicate a case in which the measured data acquired by imaging the object at a radiation dose of 50% is acquired according to an exemplary embodiment. Line t13 indicates a case in which a process of alternately estimating the ROI-outside measured data and the ROI-inside measured data according to an exemplary embodiment is performed once, and line t14 indicates a case in which the above process is performed twice.

Lines t13 and t14 respectively denote RMSE and rRMSE of a reconstructed image acquired according to the repetition number of the iterative reconstruction process, when the reconstructed image is acquired from the estimated ROI-inside measured data using the iterative reconstruction technique. For line t13, the repetition number of the iterative reconstruction process may be optimized at the number of 11.

RMSE and rRMSE may be acquired through Equation 1 and Equation 2.

$$RMSE(x) = \sqrt{\frac{1}{N_{ROI}} \sum_{i \in ROI} (x_i - x_i^{ref})^2} \quad \text{[Equation 1]}$$

$$rRMSE(x) = \frac{\sqrt{\frac{1}{N_{ROI}} \sum_{i \in ROI} (x_i - x_i^{ref})^2}}{\max(x^{ref}) - \min(x^{ref})} \times 100\% \quad \text{[Equation 2]}$$

In Equations 1 and 2, "x" denotes a reconstructed image and "$x^{ref}$" denotes a ground truth image.

Since line t14 denotes RMSE and rRMSE that are lower than line t13, it may be seen that the quality of a reconstructed image is further improved as the process of alternately estimating the ROI-outside measured data and the ROI-inside measured data according to an exemplary embodiment.

Also, since lines t13 and t14 according to an exemplary embodiment have RMSE and rRMSE that are lower than line t12 using the analytical reconstruction, the quality of an image is remarkably improved. Also, it may be seen that lines t13 and t14 in which a radiation dose is 50% have RMSE and rRMSE lower than line t11 in which a radiation dose is 100%. In other words, according to an exemplary embodiment, not only artifacts due to truncation but also errors due to low radiation dose may be overcome.

FIG. 20 is a flowchart of a method (S300) of operating a medical imaging apparatus according to an exemplary embodiment.

Referring to FIG. 20, the medical imaging apparatus may acquire measured data (S310). The medical imaging apparatus may acquire an initial image based on the measured data (S320).

The medical imaging apparatus may estimate initial ROI-inside measured data based on the measured data and the initial image (S330).

The medical imaging apparatus may estimate ROI-outside measured data based on the initial ROI-inside measured data (S340). The medical imaging apparatus may estimate the ROI-inside measured data based on a difference between the measured data and the ROI-outside measured data (S350).

The medical imaging apparatus may determine whether to update the ROI-outside measured data and the ROI-inside measured data (S360). When it is determined to update, the medical imaging apparatus may update the estimated ROI-outside measured data and the estimated ROI-inside measured data by re-performing the operations S340 and S350.

The medical imaging apparatus may perform an update operation including the updating the ROI-outside measured data and the updating the ROI-inside measured data by iteratively performing the operations S340, S350, and S360 until it is determined to stop updating in operation S360.

When the update is stopped, the medical imaging apparatus may acquire the reconstructed image based on the finally estimated ROI-inside measured data (S370).

The method S300 of operating a medical imaging apparatus of FIG. 20 may be performed by the medical imaging apparatus 300 of FIG. 8. Also, all the above descriptions may be applied to the method S300 of operating the medical imaging apparatus of FIG. 20.

FIG. 21 is a block diagram of a process in which a medical imaging apparatus acquires a reconstructed image from the measured data, according to an exemplary embodiment.

Referring to FIG. 21, the medical imaging apparatus may acquire an initial image 91 by reconstructing measured data 90 (S31).

The medical imaging apparatus may acquire initial ROI-outside RP data 91r by re-projecting (RP) the outside of ROI in the initial image 91. The medical imaging apparatus may estimate a difference between the initial ROI-outside RP data 91r and the measured data 90 as initial ROI-inside measured data 92 (S32).

The medical imaging apparatus may acquire an initial ROI-inside image 93 by reconstructing the initial ROI-inside measured data 92 (S33).

The medical imaging apparatus may acquire ROI-inside RP data 93r by re-projecting the initial ROI-inside image 93. The medical imaging apparatus may estimate a difference between the ROI-inside RP data 93r and the measured data 90 as ROI-outside measured data 94 (S34).

The medical imaging apparatus may acquire an ROI-outside image 95 by reconstructing the ROI-outside measured data 94 (S35).

The medical imaging apparatus may acquire ROI-outside RP data 95r by re-projecting the ROI-outside image 95. The medical imaging apparatus may estimate a difference between the ROI-outside RP data 95r and the measured data 90 as ROI-inside measured data 96 (S36).

The medical imaging apparatus may acquire an ROI-inside image 97 by reconstructing the ROI-inside measured data 96 (S37).

The medical imaging apparatus may determine whether to update the ROI-outside measured data and the ROI-inside measured data (S38).

When the update is determined, the medical imaging apparatus may update the ROI-outside measured data 94 based on the ROI-inside image 97, not the initial ROI-inside image 93, the ROI-inside measured data 96 based on the updated ROI-outside measured data 94, and the ROI-inside image 97 based on the updated ROI-inside measured data 96. As such, the medical imaging apparatus may iteratively perform the operations S34, S35, S36, S37, and S38 until the stop of the update is determined in the operation S38.

When it is determined to stop the updating in operation S38, the medical imaging apparatus may acquire a reconstructed image 98 based on the finally updated ROI-inside image 97.

Figure 22:
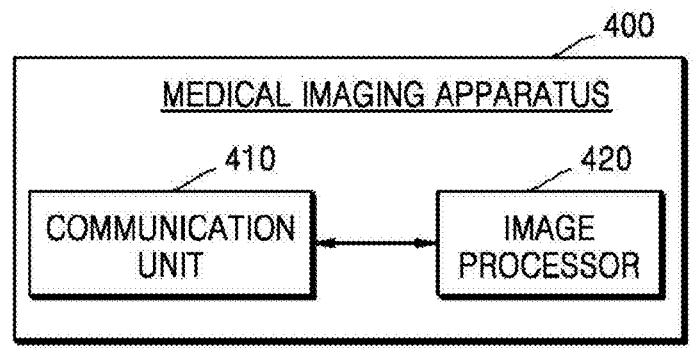
FIGS. 22 to 24 are block diagrams of structures of medical imaging apparatuses according to exemplary embodiments.

FIG. 22 is a block diagram of a structure of a medical imaging apparatus 400 according to an exemplary embodiment.

Referring to FIG. 22, the medical imaging apparatus 400 may include a communication unit 410 and an image processor 420. The communication unit 410 may be a structure corresponding to the data acquirer 310 of the medical imaging apparatus 300 of FIG. 8 or may be included in the data acquirer 310. The communication unit 410 may receive measured data from an external device. The external device may be a medical apparatus including an X-ray source, and the medical apparatus may acquire the measured data by imaging an object and transmit the measured data to the medical imaging apparatus 400.

The image processor 420 may acquire a reconstructed image from the measured data received from the communication unit 410. Since all the above descriptions may be applied to the method of acquiring a reconstructed image from the measured data, a redundant description is omitted.

Figure 23:
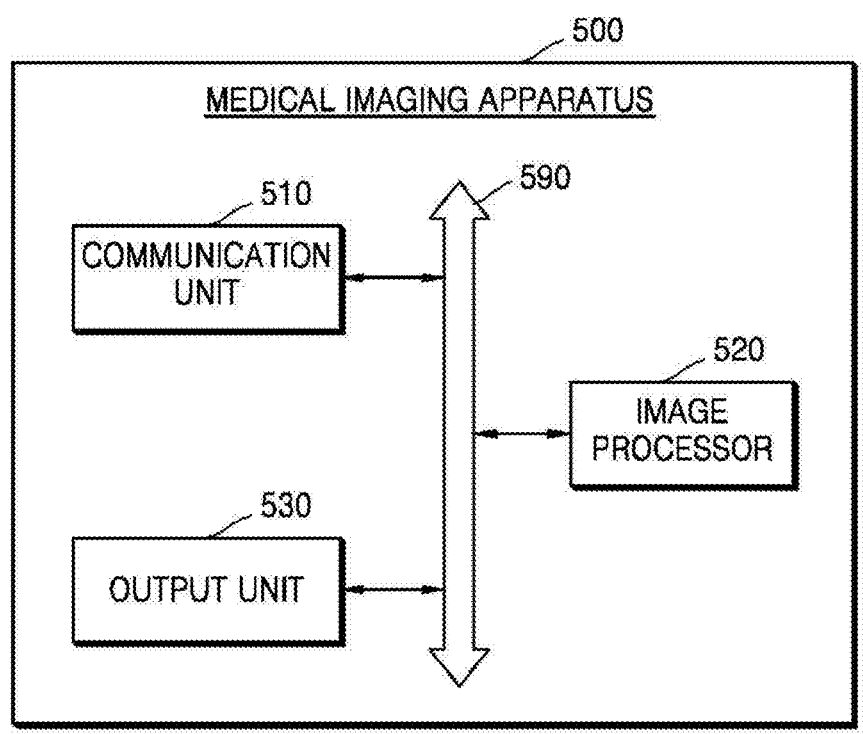

FIG. 23 is a block diagram of a structure of a medical imaging apparatus 500 according to an exemplary embodiment.

Referring to FIG. 23, the medical imaging apparatus 500 may include a communication unit 510, an image processor 520, and an output unit 530. The elements included in the medical imaging apparatus 500 may be connected to each other by a connection method 590 that may be wired or wireless.

Since the communication unit 510 and the image processor 520 of FIG. 23 respectively correspond to the communication unit 410 and the image processor 420 of FIG. 22, a redundant description is omitted.

The output unit 530 may output the reconstructed image acquired by the image processor 126 on the screen of the output unit 530. The output unit 530 may further output the data and image acquired in the process of acquiring the reconstructed image from the measured data according to an exemplary embodiment.

The output unit 530 may output information that is necessary for the user to manipulate the medical imaging apparatus 500, for example, a user interface (UI), user information, or object information. Examples of the output unit 530 may include a speaker, a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a flat panel display (FPD), a three-dimensional (3D) display, a transparent display, and other various output devices well known to one of ordinary skill in the art.

Figure 24:
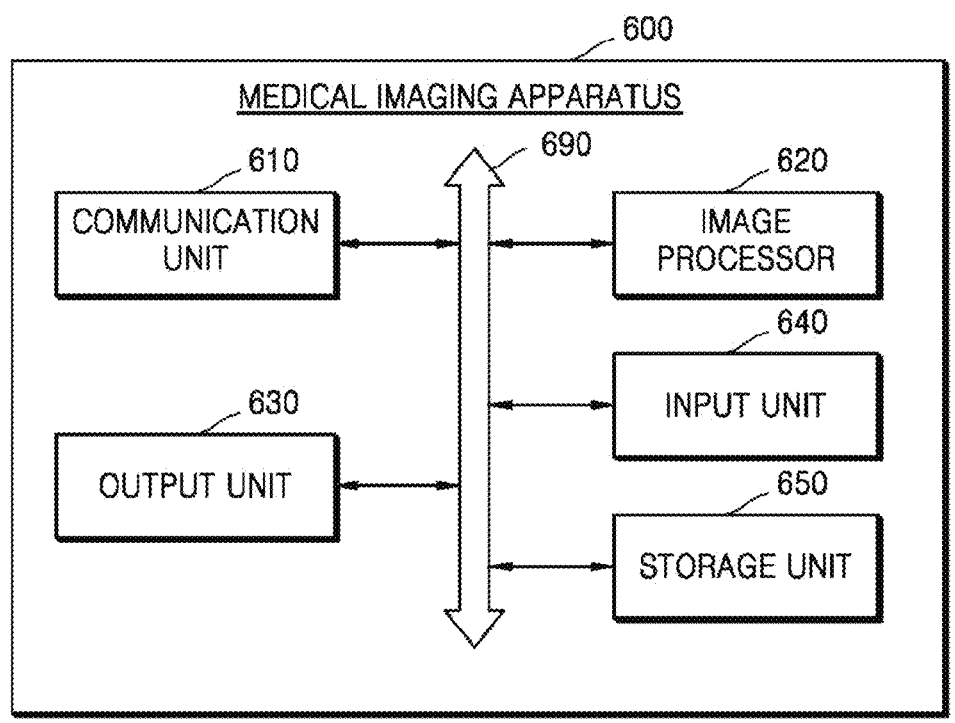

FIG. 24 is a block diagram of a structure of a medical imaging apparatus 600 according to an exemplary embodiment.

Referring to FIG. 24, the medical imaging apparatus 600 may include a communication unit 610, an image processor 620, an output unit 630, an input unit 640, and a storage unit 650. The elements included in the medical imaging apparatus 600 may be connected to each other by a connection method 690 that may be wired or wireless.

Since the communication unit 610, the image processor 620, and the output unit 630 of FIG. 24 respectively correspond to the communication unit 510, the image processor 520, and the output unit 530 of FIG. 23, a redundant description is omitted.

The input unit 640 may receive from a user a command to control the medical imaging apparatus 600. The input unit 640 may receive from a user information for determining the repetition number of update operations including updating the ROI-outside measured data and updating the ROI-inside measured data. Also, the user may set parameters related to estimation or updating the ROI-outside measured data through the input unit 640. For example, the parameter may include the size of an object or ROI-outside reconstruction parameters.

The output unit 630 and the input unit 640 may provide the user with a user interface (UI) for manipulating the medical imaging apparatus 600. The output unit 630 may output a UI.

The storage unit 650 may store various pieces of information or data for the operation of the medical imaging apparatus 600. Also, the storage unit 650 may store the data or image acquired during the process of acquiring a reconstructed image from the measured data according to an exemplary embodiment.

Figure 25:
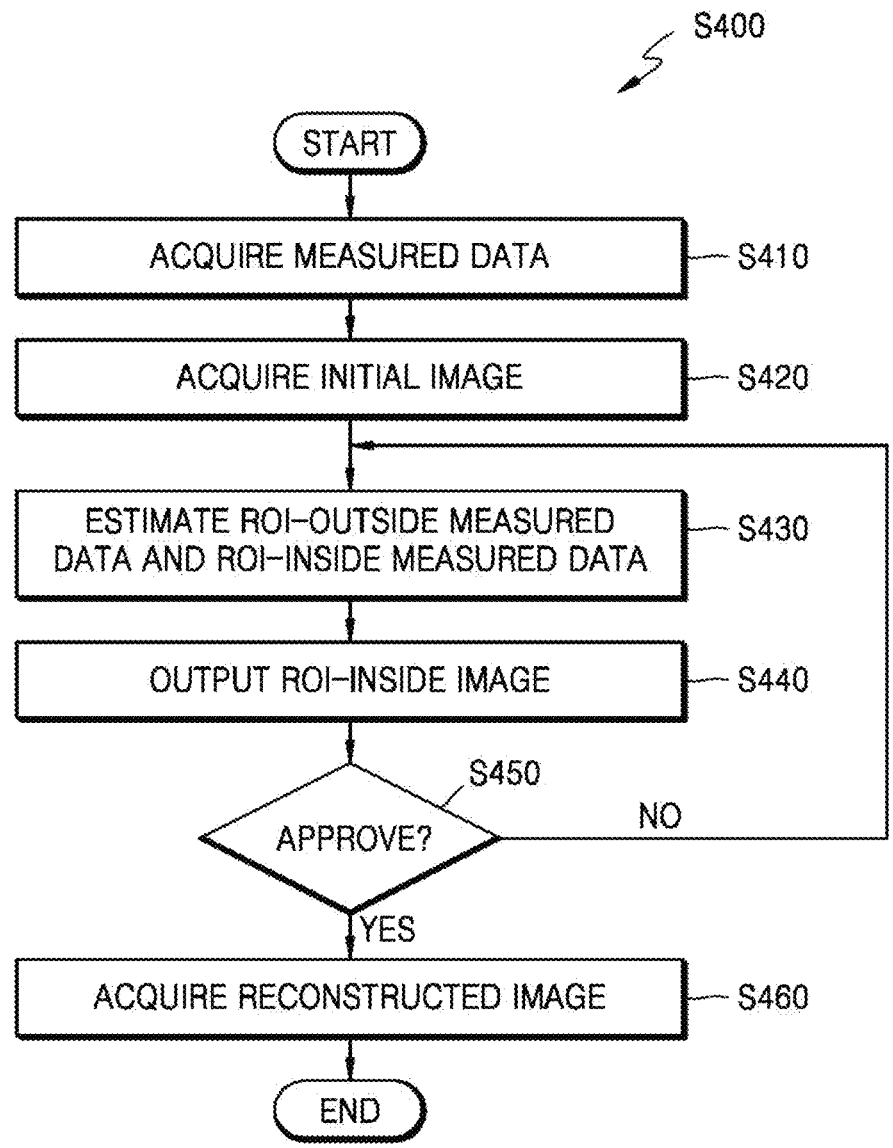
FIG. 25 is a flowchart of a method of operating a medical imaging apparatus according to an exemplary embodiment.

FIG. 25 is a flowchart of a method (S400) of operating a medical imaging apparatus according to an exemplary embodiment.

Referring to FIG. 25, the medical imaging apparatus may acquire measured data (S410). The medical imaging apparatus may acquire an initial image based on the measured data (S420).

The medical imaging apparatus may alternately estimate ROI-outside measured data and ROI-inside measured data based on the measured data and the initial image (S430). The medical imaging apparatus may output an ROI-inside image acquired based on the ROI-inside measured data (S440).

The medical imaging apparatus may receive an input of whether to approve the output ROI-inside image from the user (S450). When the approval is not input, the medical imaging apparatus may update the ROI-outside measured data and the ROI-inside measured data by re-performing the operations S430 and S440, and may output an updated ROI-inside image. The medical imaging apparatus may receive again an input of whether to approve the updated ROI-inside image from the user (S450). In other words, the medical imaging apparatus may iteratively re-perform the operations S430 to S450 until the user's approval is input.

Alternatively, if a user's input for re-performing the operations S430 and S440 or updating ROI-inside image is not inputted or a user inputs nothing, it may be assumed that the user approves the currently output ROI-inside image.

When the user's approval is input, the medical imaging apparatus stops the update operation. The medical imaging apparatus may acquire a reconstructed image based on the finally output ROI-inside image (S460).

The method (S400) of operating the medical imaging apparatus of FIG. 25 may be performed by the medical imaging apparatus 600 of FIG. 24. However, the present disclosure is not limited thereto. Also, all the above descriptions may be applied to the method (S400) of operating the medical imaging apparatus of FIG. 25.

The medical imaging apparatus according to an exemplary embodiment may be an X-ray apparatus or may be included in an X-ray apparatus.

Figure 26:
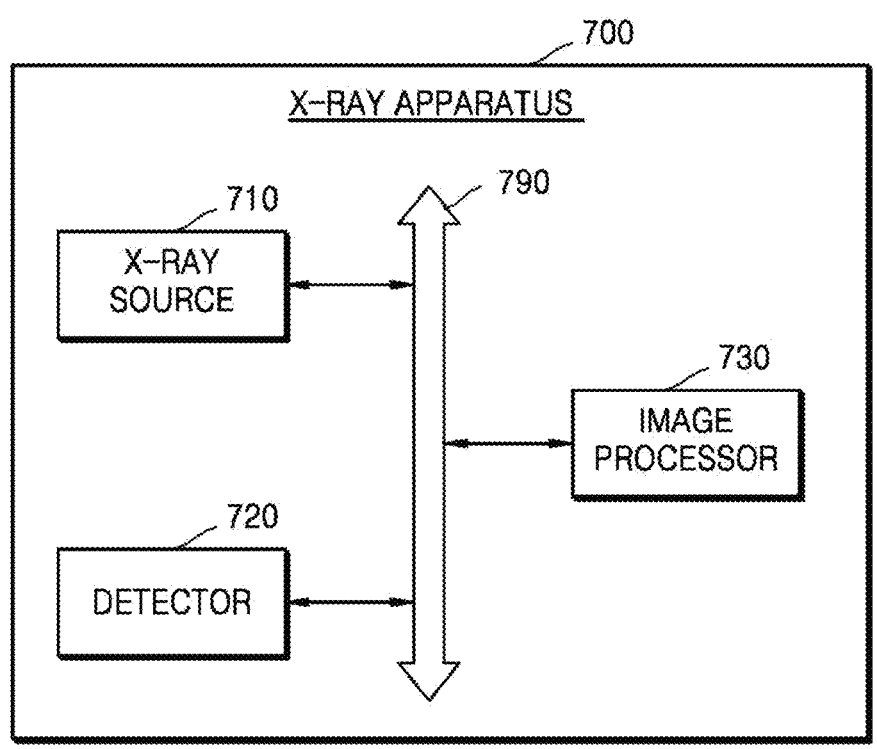
FIG. 26 is a block diagram of a structure of an X-ray apparatus according to an exemplary embodiment.

FIG. 26 is a block diagram of a structure of an X-ray apparatus 700 according to an exemplary embodiment.

Referring to FIG. 26, the X-ray apparatus 700 may include an X-ray source 710, a detector 720, and an image processor 730. The elements included in the X-ray apparatus 700 may be connected to each other by a connection method 790 that may be wired or wireless.

The X-ray apparatus 700 may acquire measured data through the X-ray source 710 and the detector 720. The image processor 730 may acquire a reconstructed image from the measured data. Since the operation of each structure is already described above, a redundant description is omitted.

In the above description, the medical imaging apparatus is described as an apparatus that is included in an X-ray apparatus or may receive the measured data by being connected to the X-ray apparatus by a wired or wireless method. However, the medical apparatus related to the medical imaging apparatus according to an exemplary embodiment is not limited to the X-ray apparatus. The method of operating a medical image according to an exemplary embodiment may be used for various medical apparatus including, for example, not only the X-ray apparatus, but also a CT apparatus, a CT apparatus for dental use, cone beam Computed Tomography (CBCT), Positron Emission Tomography (PET), Single Photon Emission Computed Tomography (SPECT), Optic Coherence Tomography (OCT), etc.

Figure 27:
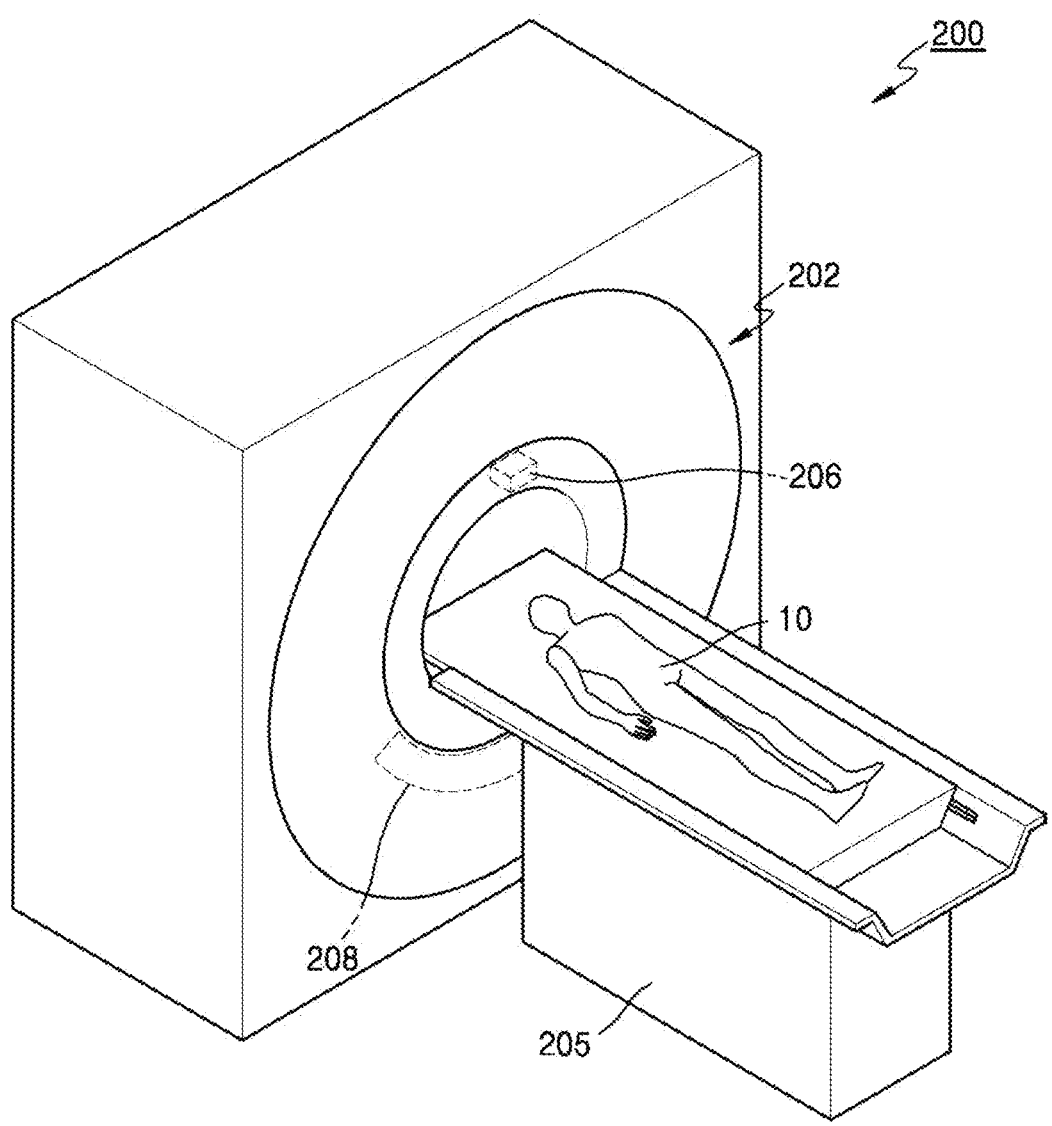
FIG. 27 is a schematic view of a CT apparatus to which an exemplary embodiment is applicable.

FIG. 27 is a schematic view of a CT apparatus 200 to which an exemplary embodiment is applicable.

Referring to FIG. 27, the CT apparatus 200 may include a gantry 202, a table 205, an X-ray source 206, and a detector 208. The gantry 202 may include the X-ray source 206 and the detector 208. The object 10 may be located on the table 205.

The table 205 may be moved in a predetermined direction, for example, at least one of upward, downward, left, and right directions, in a CT imaging process. Also, the table 205 may be rotated or tilted in a predetermined direction by a predetermined angle. The gantry 202 may also be tilted in a predetermined direction by a predetermined angle.

Figure 28:
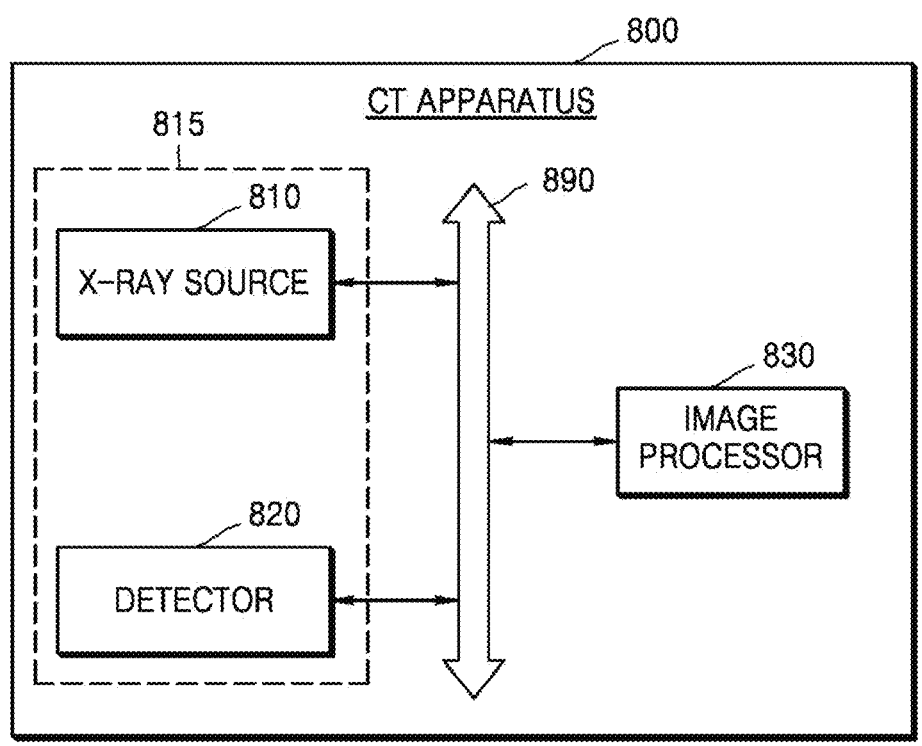
FIG. 28 is a block diagram of a structure of a CT apparatus according to an exemplary embodiment.

FIG. 28 is a block diagram of a structure of a CT apparatus 800 according to an exemplary embodiment.

Referring to FIG. 28, the CT apparatus 800 may include a gantry 815 including an X-ray source 810 and a detector 820, and an image processor 830. The elements included in the CT apparatus 800 may be connected to each other by a connection method 890 that may be wired or wireless.

The CT apparatus 800 may acquire measured data through the X-ray source 810 and the detector 820 that rotate together. The image processor 830 may acquire a reconstructed image from the measured data. Since all the descriptions may be applied to the operation of each element, a redundant description is omitted.

The exemplary embodiments of the present disclosure can be written as computer programs and can be implemented in general-use digital computers that execute the programs using a non-transitory computer readable recording medium.

Examples of the non-transitory computer readable recording medium include magnetic storage media (e.g., floppy disks, hard disks, etc.), optical recording media (e.g., CD-ROMs, DVDs, etc.), integrated circuit storage media (e.g., FLASH memory, read only memory (ROM), erasable programmable ROM (EPROM), etc.), as well as others suitable for storing computer programs.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the disclosure as defined by the following claims.

What is claimed is:

1. A medical imaging apparatus comprising:
a data acquirer configured to acquire measured data acquired by detecting X-ray transmitted by an X-ray source to an object; and
an image processor configured to:
acquire an initial image based on the measured data;
estimate a difference between data acquired by re-projecting an inside of a region of interest (ROI) in the initial image and the measured data as an ROI-outside measured data;
acquire an ROI-outside image by back-projecting the ROI-outside measured data;
estimate a difference between data acquired by re-projecting the ROI-outside image and the measured data as an ROI-inside measured data; and
acquire a reconstructed image based on the ROI-inside measured data,
wherein the image processor is further configured to alternately estimate the ROI-outside measured data and the ROI-inside measured data.

2. The medical imaging apparatus of claim 1, wherein the image processor is further configured to estimate a difference between data acquired by re-projecting an inside of an ROI in the initial image and the measured data as the ROI-outside measured data, and acquire an ROI-outside image based on the ROI-outside measured data and estimate a difference between data acquired by re-projecting the ROI-outside image and the measured data as the ROI-inside measured data.

3. The medical imaging apparatus of claim 2, wherein the image processor is further configured to acquire an ROI-inside image based on the ROI-inside measured data, determine whether to update the ROI-outside measured data and the ROI-inside measured data, and when it is determined to update the ROI-outside measured data and the ROI-inside measured data, the image processor updates the ROI-outside measured data based on the ROI-inside image, the ROI-inside measured data based on the updated ROI-outside measured data, and the ROI-inside image based on the updated ROI-inside measured data.

4. The medical imaging apparatus of claim 3, wherein the image processor is further configured to iteratively perform an update operation including updating the ROI-outside measured data, updating the ROI-inside measured data, and updating the ROI-inside image until it is determined to stop updating the ROI-outside measured data and the ROI-inside measured data, and acquire the reconstructed image based on a finally updated ROI-inside image, wherein the finally updated ROI-inside image is the ROI-inside image updated just prior to being determined to stop updating the ROI-outside measured data and the ROI-inside measured data.

5. The medical imaging apparatus of claim 4, wherein the image processor is configured to stop the update operation when a difference between the ROI-inside measured data and data acquired by re-projecting the ROI-inside image acquired based on the ROI-inside measured data is less than a threshold value.

6. The medical imaging apparatus of claim 4, wherein the image processor is configured to stop the update operation after repeating the update operation a predetermined number of times.

7. The medical imaging apparatus of claim 6, further comprising a user input unit configured to receive an input for determining the predetermined number of times.

8. The medical imaging apparatus of claim 4, further comprising:
a display configured to output at least one of the ROI-inside image and the updated ROI-inside image; and
a user input unit configured to receive an input as to whether the output ROI-inside image is approved,
wherein when the input received through the user input unit indicates that the output ROI-inside image is approved, the image processor stops the update operation.

9. The medical imaging apparatus of claim 4, further comprising an input unit configured to receive a parameter related to estimation or updating the ROI-outside measured data.

10. The medical imaging apparatus of claim 3, wherein the image processor is further configured to acquire the ROI-outside image based on the ROI-outside measured data by an iterative reconstruction technique and acquire the ROI-inside image based on the ROI-inside measured data by the iterative reconstruction technique.

11. The medical imaging apparatus of claim 3, wherein the image processor is further configured to acquire the initial image based on the measured data by using at least one of an analytical reconstruction technique and an iterative reconstruction technique.

12. The medical imaging apparatus of claim 11, wherein the image processor is further configured to acquire the initial image by removing an outside of the ROI from an image reconstructed based on the measured data.

13. The medical imaging apparatus of claim 1, wherein the image processor is further configured to estimate a difference between data acquired by re-projecting an outside of an ROI in the initial image and the measured data as initial ROI-inside measured data, acquire an initial ROI-inside image based on the initial ROI-inside measured data and estimate a difference between data acquired by re-projecting the ROI-inside image and the measured data as the ROI-outside measured data, and acquire an ROI-outside image based on the ROI-outside measured data and estimate a difference between data acquired by re-projecting the ROI-outside image and the measured data as the ROI-inside measured data.

14. The medical imaging apparatus of claim 13, wherein the image processor is configured to acquire an ROI-inside image based on the ROI-inside measured data, determine whether to update the ROI-outside measured data and the ROI-inside measured data, and when it is determined to update the ROI-outside measured data and the ROI-inside measured data, the image processor updates the ROI-outside measured data based on the ROI-inside image, the ROI-inside measured data based on the updated ROI-outside measured data, the ROI-inside image based on the updated ROI-inside measured data.

15. The medical imaging apparatus of claim 14, wherein the image processor is further configured to iteratively perform an update operation including updating the ROI-outside measured data, updating the ROI-inside measured data, and updating the ROI-inside image until it is determined to stop updating the ROI-outside measured data and the ROI-inside measured data, and acquire the reconstructed image based on a finally updated ROI-inside image, wherein the finally updated ROI-inside image is the ROI-inside image updated just prior to being determined to stop updating the ROI-outside measured data and the ROI-inside measured data.

16. The medical imaging apparatus of claim 1, wherein the measured data is at least one of truncated data and data acquired at a low radiation dose of the X-ray transmitted by the X-ray source, wherein the low radiation dose is less than a reference value.

17. The medical imaging apparatus of claim 1, further comprising an X-ray detector configured to rotate with the X-ray source and detect the X-ray.

18. The medical imaging apparatus of claim 17, further comprising a C-arm having one end connected to the X-ray source and another end connected to the X-ray detector.

19. The medical imaging apparatus of claim 17, further comprising a gantry comprising the X-ray source and the X-ray detector.

20. The medical imaging apparatus of claim 1, wherein the data acquirer comprises a communication unit configured to receive the measured data from a medical apparatus comprising the X-ray source.

21. A method of operating a medical image apparatus, the method comprising:
acquiring measured data acquired by detecting X-ray transmitted by an X-ray source to an object;
acquiring an initial image based on the measured data;
estimating a difference between data acquired by re-projecting an inside of a region of interest (ROI) in the initial image and the measured data as an ROI-outside measured data;
acquiring an ROI-outside image by back-projecting the ROI-outside measured data;
estimating a difference between data acquired by re-projecting the ROI-outside image and the measured data as an ROI-inside measured data; and
acquiring a reconstructed image based on the ROI-inside measured data,
wherein the ROI-outside measured data and the ROI-inside measured data are alternately estimated.

22. The method of claim 21, wherein estimating the ROI-outside measured data and ROI-inside measured data comprises:
estimating a difference between data acquired by re-projecting an inside of an ROI in the initial image and the measured data as the ROI-outside measured data; and
acquiring an ROI-outside image based on the ROI-outside measured data and estimating a difference between data acquired by re-projecting the ROI-outside image and the measured data as the ROI-inside measured data.

23. The method of claim 22, further comprising:
acquiring an ROI-inside image based on the ROI-inside measured data;
determining whether to update the ROI-outside measured data and the ROI-inside measured data; and
when it is determined to update the ROI-outside measured data and the ROI-inside measured data, updating the ROI-outside measured data based on the ROI-inside image, updating the ROI-inside measured data based on the updated ROI-outside measured data, and updating the ROI-inside image based on the updated ROI-inside measured data.

24. The method of claim 23, further comprising performing iteratively an update operation including updating the ROI-outside measured data, updating the ROI-inside measured data, and updating the ROI-inside image until it is determined to stop updating the ROI-outside measured data and the ROI-inside measured data, and acquire the reconstructed image based on a finally updated ROI-inside image, wherein the finally updated ROI-inside image is the ROI-inside image updated just prior to being determined to stop updating the ROI-outside measured data and the ROI-inside measured data.

25. The method of claim 24, wherein the update operation is stopped when a difference between the ROI-inside measured data and data acquired by re-projecting the ROI-inside image acquired based on the ROI-inside measured data is less than a threshold value.

26. The method of claim 24, wherein the update operation is stopped after the update operation is repeated a predetermined number of times.

27. The method of claim 26, further comprising receiving an input to determine the predetermined number of times.

28. The method of claim 24, further comprising:
outputting at least one of the ROI-inside image and the updated ROI-inside image; and
receiving an input as to whether the output ROI-inside image is approved,
wherein upon receiving the input indicating that the output ROI-inside image is approved, the update operation is stopped.

29. The method of claim 24, further comprising receiving a parameter related to estimation or updating the ROI-outside measured data.

30. The method of claim 23, wherein the ROI-outside image is acquired based on the ROI-outside measured data by an iterative reconstruction technique and the ROI-inside image is acquired based on the ROI-inside measured data by the iterative reconstruction technique.

31. The method of claim 23, wherein the initial image is acquired based on the measured data by using at least one of an analytical reconstruction technique and an iterative reconstruction technique.

32. The method of claim 21, wherein the initial image is acquired by removing an outside of an ROI from an image reconstructed based on the measured data.

33. The method of claim 21, wherein estimating the ROI-outside measured data and ROI-inside measured data comprises:
estimating a difference between data acquired by re-projecting an outside of an ROI in the initial image and the measured data as initial ROI-inside measured data;
acquiring an initial ROI-inside image based on the initial ROI-inside measured data and estimating a difference between data acquired by re-projecting the ROI-inside image and the measured data as the ROI-outside measured data; and
acquiring an ROI-outside image based on the ROI-outside measured data and estimating a difference between data acquired by re-projecting the ROI-outside image and the measured data as the ROI-inside measured data.

34. The method of claim 21, wherein the measured data is at least one of truncated data and data acquired at a low radiation dose of the X-ray transmitted by the X-ray source, wherein the low radiation dose is less than a reference value.

35. A non-transitory computer readable storage medium having stored thereon a program, which when executed by a computer, performs:
acquiring measured data acquired by detecting X-ray transmitted by an X-ray source to an object;
acquiring an initial image based on the measured data;
estimating a difference between data acquired by re-projecting an inside of a region of interest (ROI) in the initial image and the measured data as an ROI-outside measured data;
acquiring an ROI-outside image by back-projecting the ROI-outside measured data;
estimating a difference between data acquired by re-projecting the ROI-outside image and the measured data as an ROI-inside measured data; and
acquiring a reconstructed image based on the ROI-inside measured data,
wherein the ROI-outside measured data and the ROI-inside measured data are alternately estimated.

* * * * *